United States Patent
Waters et al.

(10) Patent No.: US 11,147,491 B2
(45) Date of Patent: Oct. 19, 2021

(54) SYSTEMS AND METHODS FOR BLADDER HEALTH MANAGEMENT

(71) Applicant: Verathon Inc., Bothell, WA (US)

(72) Inventors: Kendall R. Waters, Issaquah, WA (US); Si Luo, Bothell, WA (US); Joon Hwan Choi, Bothell, WA (US)

(73) Assignee: Verathon Inc., Bothell, WA (US)

( * ) Notice: Subject to any disclaimer, the term of this patent is extended or adjusted under 35 U.S.C. 154(b) by 171 days.

(21) Appl. No.: 16/198,064

(22) Filed: Nov. 21, 2018

(65) Prior Publication Data

US 2019/0150821 A1    May 23, 2019

Related U.S. Application Data

(60) Provisional application No. 62/589,881, filed on Nov. 22, 2017.

(51) Int. Cl.
*A61B 5/20* (2006.01)
*A61B 5/00* (2006.01)
(Continued)

(52) U.S. Cl.
CPC ............ *A61B 5/204* (2013.01); *A61B 5/0059* (2013.01); *A61B 5/0082* (2013.01); *A61B 5/1073* (2013.01); *A61B 5/1079* (2013.01); *A61B 5/1112* (2013.01); *A61B 5/1123* (2013.01); *A61B 5/4866* (2013.01); *A61B 5/681* (2013.01); *A61B 5/6833* (2013.01); *A61B 5/7246* (2013.01); *A61B 5/7264* (2013.01); *A61B 5/7282* (2013.01); *A61B 5/7405* (2013.01); *A61B 5/746* (2013.01); *A61B 5/7425* (2013.01); *A61B 8/08* (2013.01); *A61B 8/4227* (2013.01);
(Continued)

(58) Field of Classification Search
None
See application file for complete search history.

(56) References Cited

U.S. PATENT DOCUMENTS

| 6,579,247 B1 | 6/2003 | Abramovitch et al. |
| 7,522,061 B2 | 4/2009 | Rondoni et al. |
| (Continued) | | |

FOREIGN PATENT DOCUMENTS

| WO | 2014067248 A1 | 5/2014 |
| WO | 2016030960 A1 | 3/2016 |
| WO | 2017017426 A1 | 2/2017 |

OTHER PUBLICATIONS

Partial International Search Report issued in corresponding International Application No. PCT/US2018/062250, dated Feb. 28, 2019, 14 pages.
(Continued)

*Primary Examiner* — Paula J Stice
(74) *Attorney, Agent, or Firm* — Snyder, Clark, Lesch & Chung, LLP

(57) ABSTRACT

A system includes at least one wearable device configured to monitor a bladder volume of a user associated with the at least one wearable device, monitor moisture associated with the user, and transmit information regarding the bladder volume and moisture. The system also includes a display device configured to receive the information regarding the bladder volume and moisture from the at least one wearable device, and display information to the user based on the received information.

21 Claims, 20 Drawing Sheets

(51) Int. Cl.
  *A61B 5/11* (2006.01)
  *A61B 8/08* (2006.01)
  *A61B 8/00* (2006.01)
  *A61B 5/107* (2006.01)
  *A61F 13/42* (2006.01)
  *A61B 90/00* (2016.01)
  *G06F 1/16* (2006.01)
  *G16H 50/20* (2018.01)
  *G16H 40/63* (2018.01)
  *G16H 50/50* (2018.01)
  *G16H 20/60* (2018.01)
  *A61B 8/14* (2006.01)
  *A61B 5/053* (2021.01)

(52) U.S. Cl.
  CPC .......... *A61B 8/4472* (2013.01); *A61B 8/5223* (2013.01); *A61B 8/56* (2013.01); *A61B 90/361* (2016.02); *A61F 13/42* (2013.01); *G06F 1/163* (2013.01); *G16H 20/60* (2018.01); *G16H 40/63* (2018.01); *G16H 50/20* (2018.01); *G16H 50/50* (2018.01); *A61B 5/053* (2013.01); *A61B 5/1116* (2013.01); *A61B 5/208* (2013.01); *A61B 5/6804* (2013.01); *A61B 5/6831* (2013.01); *A61B 5/742* (2013.01); *A61B 8/14* (2013.01); *A61B 8/483* (2013.01); *A61F 2013/424* (2013.01)

(56) References Cited

U.S. PATENT DOCUMENTS

| | | |
|---|---|---|
| 7,661,307 B1 | 2/2010 | Milone |
| 8,398,553 B2 | 3/2013 | Kristiansen |
| 9,061,146 B2 | 6/2015 | Gerber |
| 10,412,208 B1* | 9/2019 | Minoo ................ H04M 19/047 |
| 2007/0252713 A1 | 11/2007 | Rondoni et al. |
| 2007/0255176 A1 | 11/2007 | Rondoni et al. |
| 2008/0004679 A1 | 1/2008 | Naghavi et al. |
| 2008/0266117 A1* | 10/2008 | Song ....................... A61F 13/42 |
| | | 340/573.5 |
| 2012/0179665 A1 | 7/2012 | Baarman et al. |
| 2016/0120455 A1 | 5/2016 | Pop et al. |
| 2016/0174866 A1 | 6/2016 | Chan |
| 2016/0175164 A1 | 6/2016 | Mashin-Chi et al. |
| 2017/0065821 A1 | 3/2017 | Brink et al. |
| 2017/0263102 A1 | 9/2017 | Tshilombo et al. |
| 2018/0008185 A1* | 1/2018 | Ramu .................... A61B 5/204 |

OTHER PUBLICATIONS

Design of a Noninvasive Bladder Urinary Volume Monitoring System Based on Bio-Impedance by Li et al. (Engineering, 2013, 5, 321-325).

Novioscan wearable untrasound care. Retrieved online at http://novioscan.nl/. Accessed Nov. 27, 2018, 5 pages.

Ozmo Smart Bottle. Retrieved online at https://www.ozmo.io/. Accessed Nov. 27, 2018, 5 pages.

Rodger wireless bed-wetting alarm system. Accessed Nov. 27, 2018. Retrieved online at https://bedwettingstore.com/rodger-wireless-bedwetting-alarm.html, 6 pages.

K. Keerthi: Noninvasive Optical Monitoring of Bladder Filling to Capacity Using a Wireless Near Infrared Spectroscopy Device, 17 pages. Accessed Nov. 27, 2018. Retrieved online at https://www.slideshare.net/KeerthiKancharia/monitoring-of-bladder-filling-to-capacity.

* cited by examiner

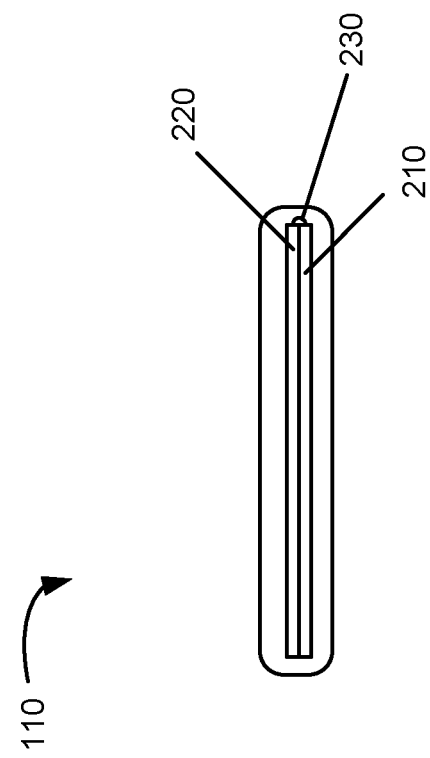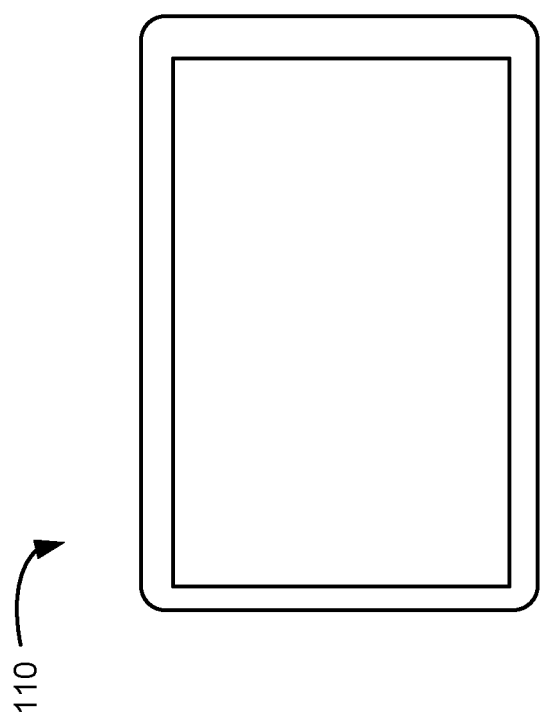

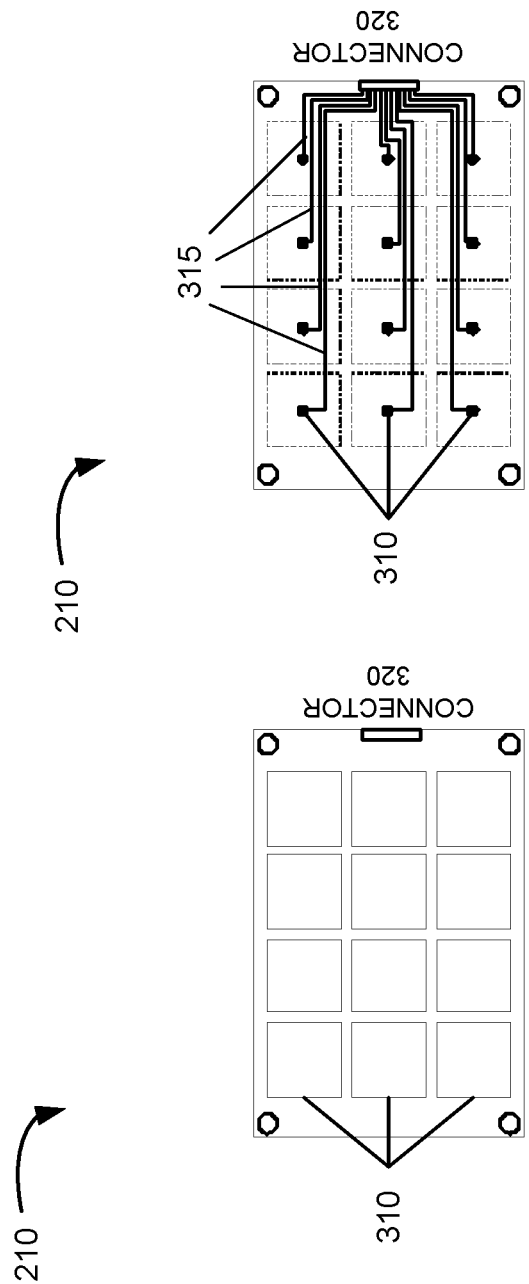

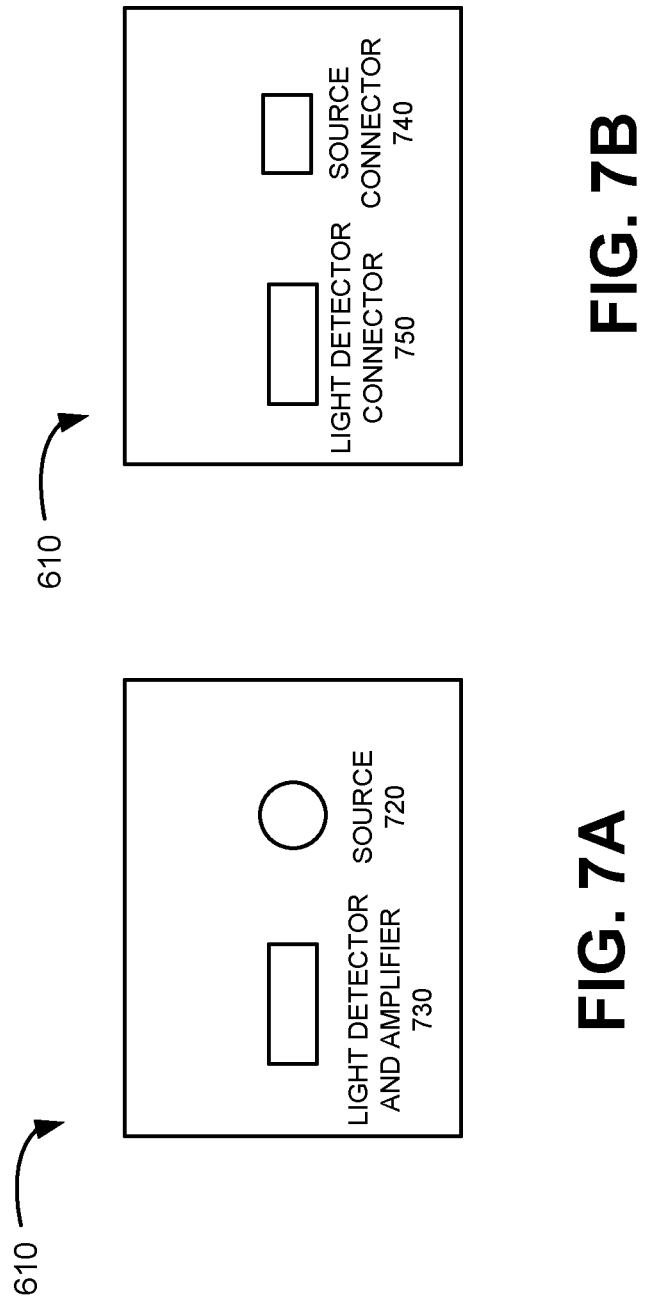

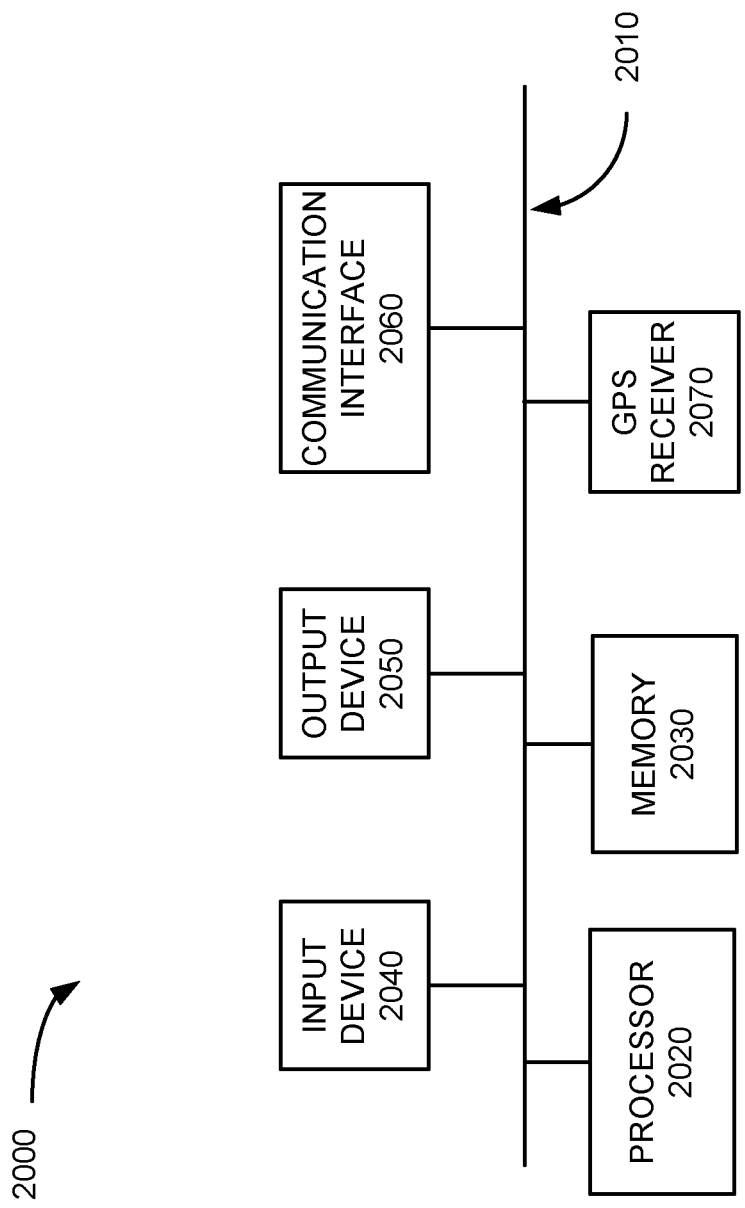

SYSTEMS AND METHODS FOR BLADDER HEALTH MANAGEMENT

RELATED APPLICATION

This application claims priority under 35 U.S.C. § 119 based on U.S. Provisional Application No. 62/589,881 filed Nov. 22, 2017, the contents of which are hereby incorporated herein by reference in their entirety.

BACKGROUND INFORMATION

Millions of people in the United States and around the world suffer from urinary incontinence (UI) or accidental urinary leakage. In particular, it has been estimated that nearly a third of women over the age of 50 suffer from accidental urinary leakage. Accidental urinary leakage may affect quality of life, lead to lifestyle changes (e.g., use of adult diapers), and result in potentially more involved treatment (e.g., minimally invasive surgery).

Causes of UI may be determined through a detailed assessment of a patient's UI and using a food diary to track intake. Treatment strategies for UI often depend on the particular causes. In addition, conventional UI assessments and toileting programs typically require active participation of a caregiver. Further, maintaining compliance to a toileting program is a challenge for most people.

BRIEF DESCRIPTION OF THE DRAWINGS

FIGS. 2A and 2B illustrate a top view and side sectional view of a bladder volume monitoring device in accordance with an exemplary implementation;

FIGS. 3A and 3B illustrate a top view and a bottom view of an exemplary ultrasound sensor included in a bladder volume monitoring device in accordance with an exemplary implementation;

FIGS. 7A and 7B illustrate a top view and bottom view of a near-infrared based sensor in accordance with an exemplary implementation;

FIG. 20 is a block diagram illustrating exemplary components that may be implemented in one or more devices associated with bladder health management in accordance with exemplary implementations.

DETAILED DESCRIPTION OF PREFERRED EMBODIMENTS

Figure 1B:
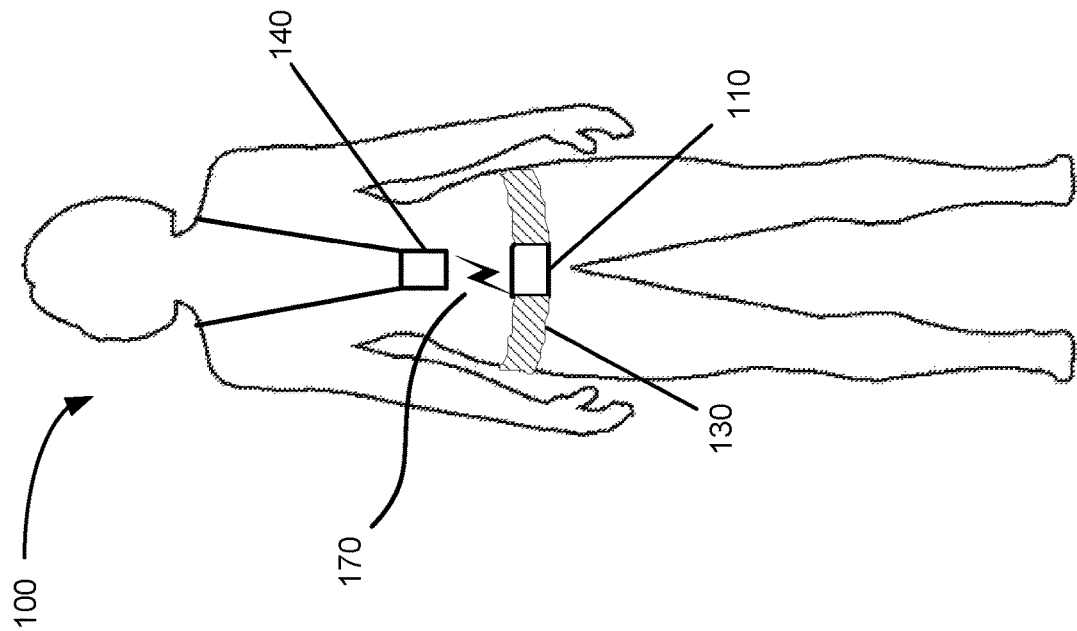
FIGS. 1A and 1B illustrate exemplary bladder monitoring devices attached to or worn by users.

The following detailed description refers to the accompanying drawings. The same reference numbers in different drawings may identify the same or similar elements. Also, the following detailed description does not limit the invention.

Implementations described herein include a multi-sensor system that provides automated monitoring of the bladder and bladder-related incidents that can be used to assess and/or manage UI. In one implementation, a multi-sensor system includes one or more wearable devices that are capable of bladder volume monitoring, moisture monitoring, and patient location monitoring. The wearable device may be battery powered or may receive power from a separate battery-powered display. In one implementation, the multi-sensor system may include an ultrasound-based device having at least one ultrasound transducer, transmit and receive circuitry, a processor to analyze signals from the ultrasound transducer for monitoring bladder volume, and an antenna to transmit and receive information.

In another implementation, the multi-sensor system may also include a near-infrared based device having a near-infrared light source, a near-infrared light detector, a processor to analyze signals from the near-infrared light detector for monitoring bladder volume, and an antenna to transmit and receive information.

In other implementations, the multi-sensor system may include a bioelectrical impedance device having a low radio frequency source, multiple excitation electrodes, multiple measurement electrodes, a processor to analyze measured signals from the multiple electrodes for monitoring bladder volume, and an antenna to transmit and receive information.

In some implementations, the multi-sensor system may include a device having a sensor and a processor for detecting and analyzing moisture and an antenna to transmit and receive information regarding the moisture. The multi-sensor system may also include a device including a position sensor that is able to detect and monitor location of patient.

In some implementations, the multi-sensor system displays information from at least one sensor, transmits and receives output from at least one sensor, and provides notifications based on bladder volume information and/or time.

In still other implementations, the multi-sensor system includes a drinking cup that includes a sensor to measure fluid level, a processor to analyze fluid intake, and an antenna to transmit and receive information regarding the fluid intake. In some implementations, the multi-sensor system may include a smart phone or other mobile device that captures pictures and/or videos of food and drinks, determines food/drink types and performs a volume estimation based on the analysis of pictures and/or videos. The smart phone can also estimate the ingredients of food and drinks based on the analysis of pictures and/or videos.

Still further, the multi-sensor system may also include a motion detection sensor and associated algorithms that are able to detect and classify different types of motion patterns that can trigger the stress associated with urinary incontinence, e.g., laughing, coughing, jumping etc. In another implementation, the multi-sensor system may assess bladder function by recording urinary incontinence episodes and voiding times, recording the volume and ingredients of intake liquid and foods, monitoring and guiding a scheduled voiding program, monitoring and guiding a prompted voiding program, and monitoring events that trigger the involuntary leakage of urine.

Figure 1A:
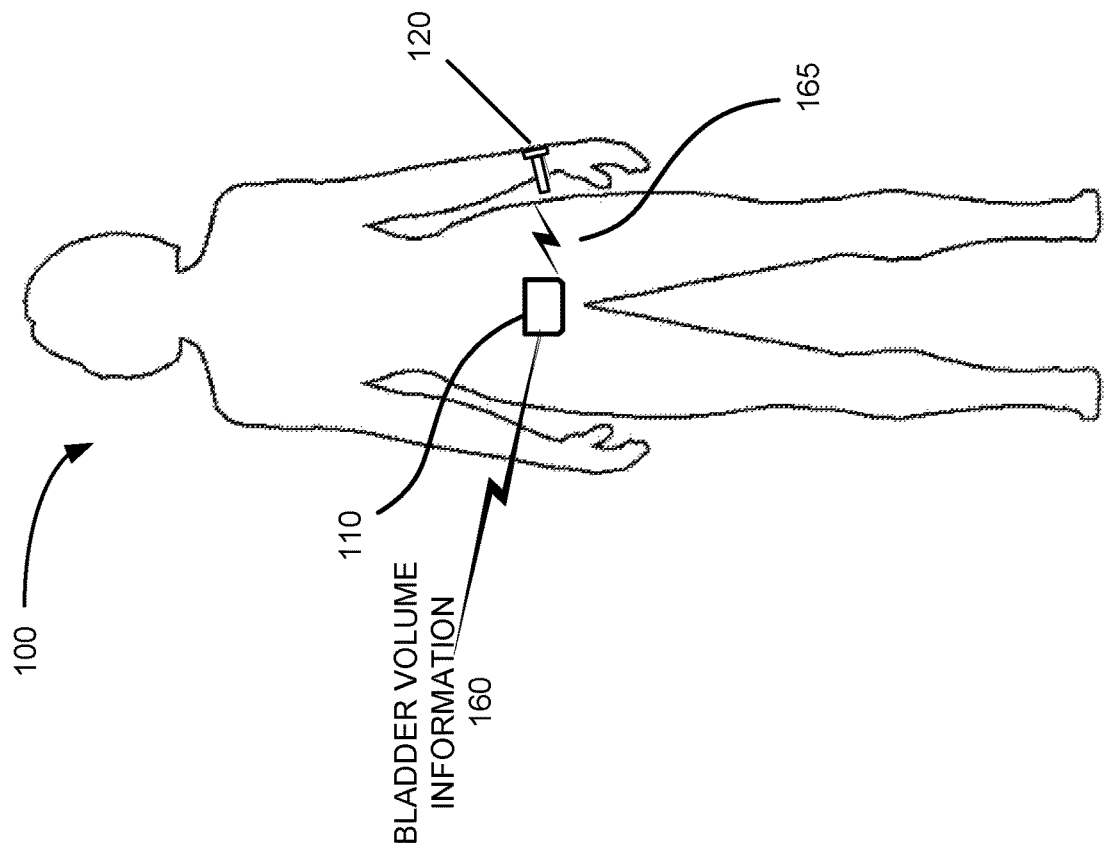

FIG. 1A illustrates a patient 100, a wearable bladder volume measurement (BVM) device 110 (also referred to as BVM 110 or device 110) and a bladder health wristband 120 (also referred to herein as wristband 120) in accordance with an exemplary implementation. FIG. 1B illustrates patient 100, BVM device 110 attached to or included with a belt 130 and a bladder health display lanyard 140 (also referred to as lanyard 140) according to another implementation.

BVM device 110 (also referred to as a "wearable bladder monitoring device," or simply as "device 110") may be attached to patient 100 using an adhesive, embedded within a garment (e.g., underwear), integrated with a belt, or another positioning mechanism. In some implementations, BVM device 110 may use an adhesive or other attachment mechanism to maintain a proper position on patient 100's abdomen (e.g., directly over a patient's bladder). BVM device 110 may provide a wearable form factor to continuously monitor bladder volume. For example, BVM device 110 may include one or more sensors to detect bladder fullness. In various implementations, different sensors in BVM device 110 may scan along different lines and may determine a volume of patient 100's bladder. Sensors for BVM device 110 may include ultrasound sensors, bio-impedance sensors, bio-reactance sensors, radio frequency (RF) sensors, infrared sensors, etc. In contrast with a conventional ultrasound bladder scanner having a relatively large ultrasound probe, BVM device 110 may generate a small number of sensing beams (e.g., acoustic beams, etc.) to identify different fluid levels in a bladder.

In one implementation, sensors in BVM device 110 may be provided with a default configuration that can be adjusted or customized. For example, sensors in BVM device 110 may be programmed to adjust the characteristics of RF signals, such as the carrier frequency, acoustic intensity, steering angle (for array transducer), pulse repeating frequency (PRF), signal bias, gain level, pre-processing method, etc., in achieving the optimal performance for each individual patient. For example, BVM device 110 may have different operating parameters for a large adult as opposed to a smaller adult/child, a male patient versus a female patient, etc.

In an exemplary implementation, BVM device 110 enables monitoring of bladder volume for patient 100. BVM device 110 is also configured to transmit bladder volume information to other devices/systems. For example, BVM device 110 may transmit bladder volume information via wireless signal 160 in FIG. 1A to an external device (not shown) which may be associated with a caregiver. BVM device 110 may also transmit bladder volume information to wristband 120 as illustrated by wireless signal 165 in FIG. 1A. In the implementation illustrated in FIG. 1B, BVM device 110 may transmit bladder volume information to lanyard 140 via wireless signals 170. Wristband 120 may be worn around patient 100's wrist or be carried elsewhere by patient 100. Display lanyard 140 may be worn around patient 100's neck as illustrated in FIG. 1B or carried elsewhere (e.g., in a shirt pocket) by patient 100.

Bladder health wristband 120 and bladder health display lanyard 140 may each include a wearable computer device that includes a transceiver, processor, memory, etc., and is able to receive bladder volume information from BVM device 110, detect patient location, and display relevant bladder health information, including bladder size, day, and time. Knowledge of patient location (e.g., within a long-term care facility or home) may help assessment and management of UI, as described in detail below. Wristband 120 and display lanyard 140 each may provide audible, visible, and/or tactile notifications to patient 100. In some implementations, wristband 120 and lanyard 140 may generate and transmit alert signals to a caregiver.

BVM device 110 may communicate with wristband 120, lanyard 140 and other external devices via a communication interface, such as a Wi-Fi interface, a Bluetooth wireless interface, a radio-frequency identification (RFID) interface, a near-field communications (NFC) wireless interface, an infra-red (IR) communications interface, and/or any other type of short-range wireless interface to exchange data. In such implementations, both BVM device 110 and wristband 120/lanyard 140 may include these communication interfaces to facilitate wireless communications. Additionally or alternatively, BVM device 110 may be connected to wristband 120 or lanyard 140 via a physical connection, such as a universal serial bus (USB) or a lightning cable.

Although FIGS. 1A and 1B illustrate exemplary components of a bladder monitoring system, in other implementations, the bladder monitoring system may include fewer components, different components, additional components, or differently-arranged components than depicted in FIGS. 1A and 1B. For example, FIGS. 1A and 1B illustrate a wristband 120 and lanyard 140 communicating with BVM device 110. In other implementations, BVM device 110 may communicate with an earpiece, lapel brooch or other wearable computer device equipped with communication functionality (e.g., wired or wireless). In still other implementations, BVM device 110 may communicate with a smart phone, tablet, or another portable computing or communication device.

Additionally or alternatively, one or more components of the bladder monitoring system may perform one or more tasks described as being performed by one or more other components of the bladder monitoring system. For example, in one implementation, BVM device 110 and wristband 120 or lanyard 140 may be combined in a single component.

FIGS. 2A and 2B illustrate a top view and side view, respectively, of BVM device 110 in accordance with an exemplary implementation. Referring to FIG. 2A, BVM device 110 may be generally rectangular in shape and have a size ranging from about 2-4 inches in length, 1-2.5 inches in width and 0.3 to 0.6 inches in thickness (e.g., 3 inches in length, 2 inches in width and 0.5 inches in thickness). Referring to FIG. 2B, BVM device 110 may include an ultrasound sensor 210, system electronics 220 and connection 230. Connection 230 may be a cable or internal connection/bus that connects ultrasound sensor 210 with system electronics 220. As described above, ultrasound sensor 210 may transmit ultrasound signals and receive ultrasound echoes associated with patient 100's bladder. System electronics 220 may receive the reflected or echo signals and estimate bladder volume based on the received echo signals.

In an exemplary implementation, ultrasound sensor 210 includes at least one ultrasound transducer element. The transducer element may be made of a piezoelectric material (e.g., lead zirconate titanate (PZT), lead magnesium niobate-lead titanate (PMN-PT), a piezocomposite material (e.g., PZT and polyurethane interstitial material), or a microelectromechanical system (MEMS) design (e.g., piezoelectric micromachined ultrasound transducer or capacitive micromachined ultrasound transducer).

In one embodiment of BVM device 110, ultrasound sensor 210 includes an array of 12 PZT elements. For example, FIGS. 3A and 3B illustrate a top view and bottom view, respectively, of ultrasound sensor 210. Referring to FIG. 3A, ultrasound sensor 210 includes 12 transducer elements 310 having a substantially square shape and a connector 320. As illustrated in FIG. 3B, each of transducer elements 310 is wired to connector 320. Transducer elements 310 may further include a matching layer (e.g., silver-loaded epoxy) and a backing layer (e.g., silver and tungsten loaded epoxy). Transducer elements 310 may be electrically connected to system electronics 220 by electrical conductors 315 and connector 320. In one implementation, transducer elements 310 are configured to transmit ultrasound signals having a nominal center frequency between 2.5 megaHertz (MHz) and 3.5 MHz.

Figure 4:
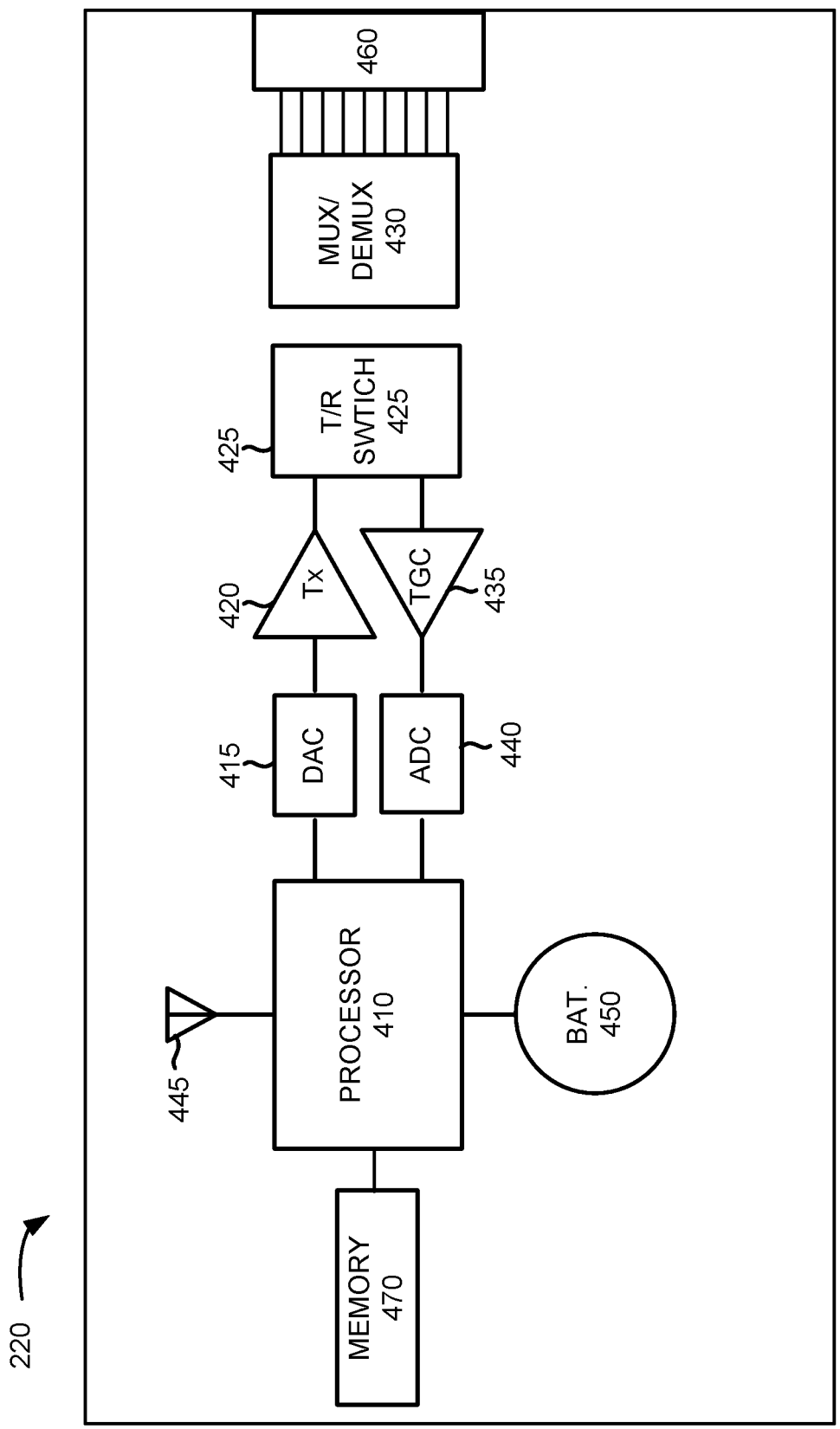
FIG. 4 illustrates components of the ultrasound sensor system electronics of FIG. 2B in accordance with an exemplary implementation.

Referring back to FIG. 2B, systems electronics 220 may receive information from ultrasound sensor 210 via connection 230. FIG. 4 illustrates components of ultrasound sensor system electronics 220 of FIG. 2B in accordance with an exemplary implementation. Referring to FIG. 4, system electronics 220 includes a processor 410, (e.g., field programmable gate array (FPGA) or advanced reduced instruction set computing (RISC) machine (ARM) microcontroller), a digital-to-analog converter (DAC) 415, a transmitter (Tx) 420, a transmit/receive (T/R) switch 425, a multiplexer/demultiplexer 430, time-gain compensation (TGC) circuitry 435, and an analog-to-digital converter (ADC) 440. System electronics 220 may further include antenna 445 to transmit and receive information, a battery 450 to provide power for components of system electronics 220, connector 460 and memory 470. In some implementations, system electronics 220 may also include a display/output and an input mechanism (not shown in FIG. 4).

Processor 410 controls the transmit and receive sequence of the ultrasound transducers 310 (shown in FIG. 3A), the processing of the received ultrasound signals to calculate bladder volume information, and the wireless transmission and reception of bladder-related information. The calculated bladder volume information may include a quantitative bladder volume (e.g., reported in milliliters (mL)) or a qualitative bladder volume (e.g., low, moderate, high).

In some implementations, processor 410 may adjust the characteristics of ultrasound transducers 310, such as a center frequency for ultrasound transducers 310 (e.g., lower frequency for heavier patient), the steering angles for ultrasound transducers 310 to modify a field of view based on patient dimensions (e.g., use a narrower field of view for smaller patient); and/or the rate of monitoring to account for different patient conditions (e.g., increase rate of monitoring depending on type of urinary incontinence).

Processor 410 may also include logic to decide if an alert (e.g., for a full or nearly full bladder) should be issued and transmitted to wristband 120 or lanyard 140. In another implementation, processor 410 may provide bladder volume readings or raw signal data to wristband 120 or lanyard 140 for use in determining if an alert should be issued. In still another implementation, processor 410 may perform a periodic system check to confirm proper operations of BVM device 110, such as whether BVM device 110 is properly located, transducers 310 are operating properly based on readings being within predetermined ranges, etc.

According to one implementation, memory 470 may store instructions, such as instructions used by processor 410 to customize BVM device 110 for a particular patient. As described above, in some implementations, system electronics 220 may include a display/output to display information to the user, such as a liquid crystal display (LCD) screen, a speaker, one or more light emitting diodes (LEDs), a vibration motor, etc. As also described, in some implementation, system electronics 220 may include an input unit that permits a user to input information to BVM device 110, such as a keypad, a button, a switch, etc. In one implementation, an input unit may be combined with an output unit as a touch-sensitive display.

Although FIG. 4 shows exemplary components of system electronics 220, in other implementations, system electronics 220 may include fewer components, different logical components, or additional logical components than depicted in FIG. 4. Additionally, other sensor types and corresponding hardware/software may be used in system electronics 220.

Figure 5:
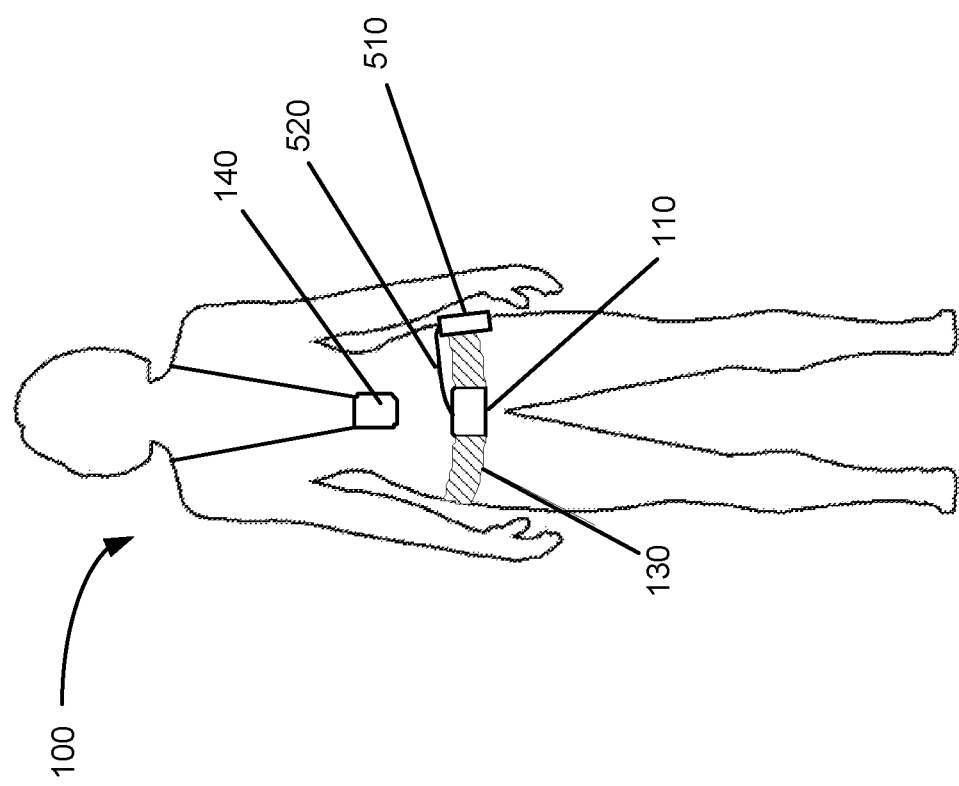
FIG. 5 illustrates a bladder monitoring device that is externally powered according to another exemplary implementation.

As described above, in some implementations, BVM device 110 may be part of an elastic belt 130 as illustrated in FIG. 1B. In addition, in some implementations, as illustrated in FIG. 5, BVM device 110 may be powered from an external power source 510, such as a separate battery or battery-powered display. In this case, BVM device 110 that is part of belt 130 may be connected to external power source 510 via power supply cable 520.

As described above, BVM device 110 may include ultrasound sensors used to transmit ultrasound signals toward the bladder and estimate the bladder size/fullness based on the received echo signals. In other implementations, other types of sensors and corresponding hardware/software may be used to measure bladder fullness.

Figure 6B:
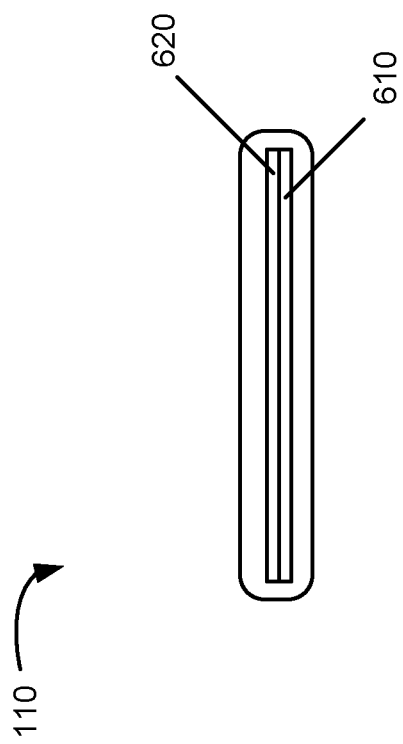
FIGS. 6A and 6B illustrate a top view and side sectional view of a bladder volume monitoring device in accordance with another exemplary implementation.
Figure 6A:
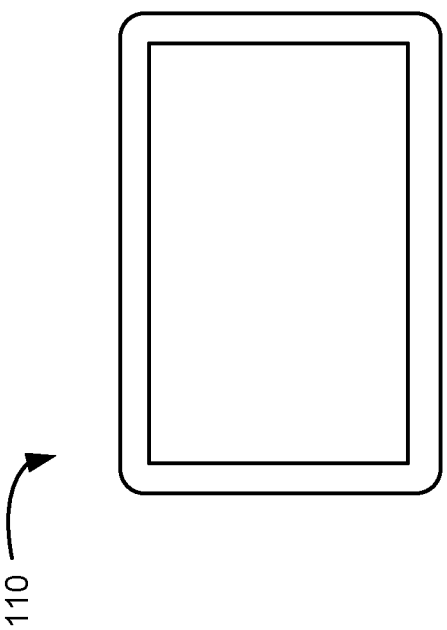

For example, in one implementation, BVM device 110 may include a near-infrared based sensor and system electronics. FIGS. 6A and 6B illustrate a top view and side view, respectively, of BVM device 110 using near-infrared sensor(s) to detect bladder fullness. In this implementation, BVM device 110 may be generally rectangular in shape and have a size ranging from about 2-4 inches in length, 1-2.5 inches in width and 0.3 to 0.6 inches in thickness (e.g., 3 inches in length, 2 inches in width and 0.5 inches in thickness). Referring to FIG. 6B, BVM device 110 may include a near-infrared sensor 610 and system electronics 620. A connection (not shown in FIG. 6B), such as a cable or internal bus, may interconnect near-infrared sensor 610 and system electronics 620. The near-infrared based BVM device 110 measures bladder volume by monitoring near-infrared light absorption due to water-based urine.

As illustrated in FIG. 7A, in one implementation, near-infrared sensor 610 includes a light source 720 and a light detector 730. In an exemplary implementation, near-infrared light source 730 transmits radiation having wavelengths ranging from approximately 700 nanometers (nm) to 2,500 nm. In one particular implementation, the wavelength is approximately 950 nm. Light detector 730 may include a silicon photodiode that is sensitive over wavelengths of approximately 350 nm and 1,100 nm (or higher). In one implementation, light detector 730 may also include a transimpedance amplifier to generate a useful output voltage. Light source 720 and light detector 730 may be electrically connected to system electronics 620 by electrical conductors and connectors, illustrated in FIG. 7B. For example, light source 720 may connect to system electronics 620 via source connector 740 and light detector 730 may connect to system electronics 620 via light detector connector 750.

Figure 8:
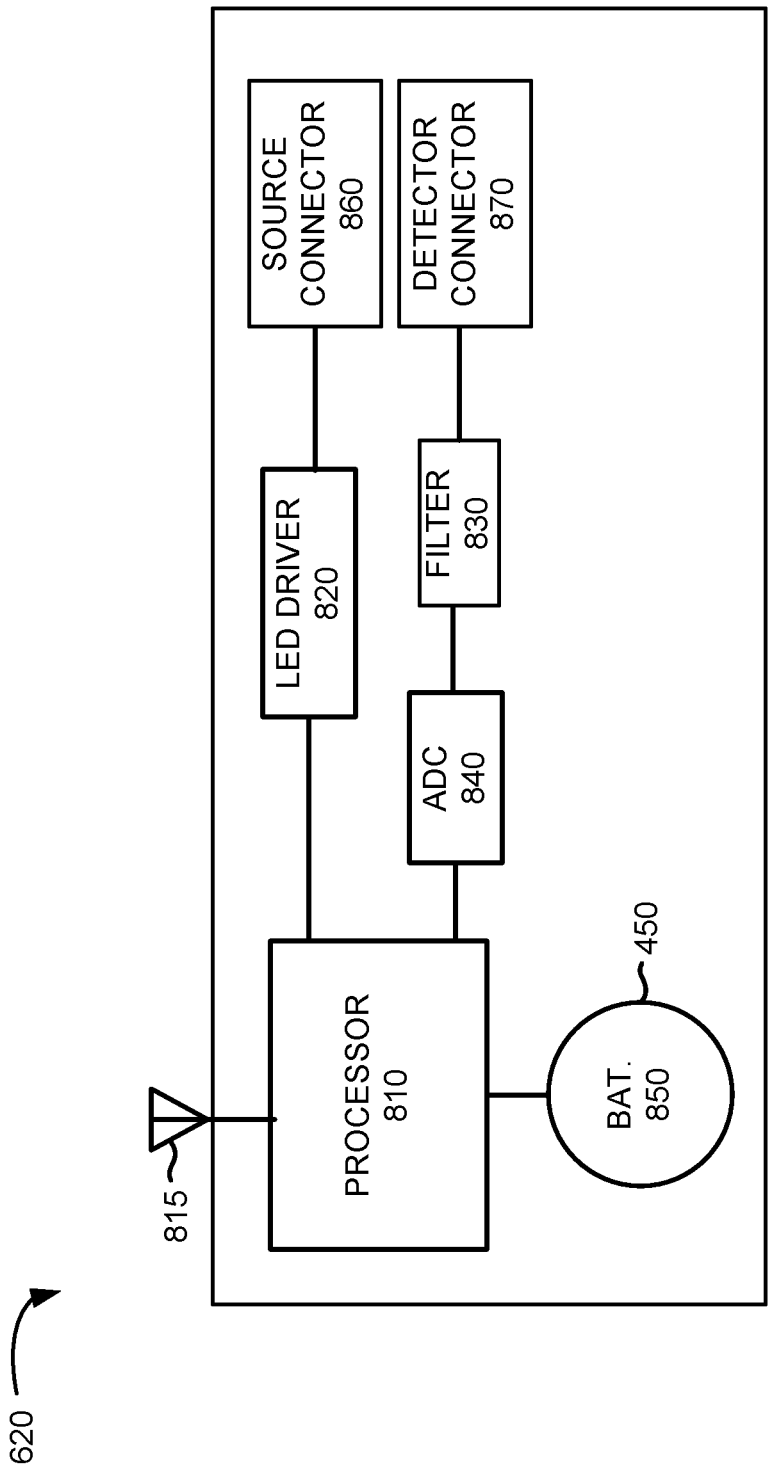
FIG. 8 illustrates components of the near-infrared system electronics of FIG. 6B in accordance with an exemplary implementation.

FIG. 8 illustrates exemplary components of near-infrared system electronics 620. Referring to FIG. 8, near-infrared system electronics 620 includes processor 810 (e.g., FPGA or ARM microcontroller), antenna 815, an LED driver 820, filter circuitry 830, an analog-to-digital converter (ADC) 840, battery 850, source connector 860 and detector connector 870. LED driver 820 may include a constant current source to maintain a substantially constant light output. Filter circuitry 830 may include a low-pass filter to remove spurious high-frequency signals. Antenna 815 may transmit and receive information. Battery 850 provides power for system electronics 620. Processor 810 controls the driving of light source 720, the processing of the received light signal voltages to estimate bladder volume information, and the wireless transmission and reception of bladder-related information. The calculated bladder volume information may include a quantitative bladder volume (e.g., reported in mL or cc) or a qualitative bladder volume (e.g., low, moderate, high).

In still another implementation, BVM device 110 includes a bioelectrical impedance sensor (not shown), instead of an ultrasound sensor or near-infrared sensor. In this implementation, the bioelectrical impedance based BVM device 110 is able to measure bladder volume by monitoring the electrical impedance of urine. The bioelectrical impedance sensor may include two or more excitation electrodes, two or more measurement electrodes, a voltage signal generator (e.g., 50 kHz frequency), and a gain phase detector. In this scenario, impedance is expected to decrease with increasing urine volume and a processor similar to processor 810 is able to measure or estimate the bladder volume based on the impedance.

In some implementation, BVM device 110 includes a motion detection sensor (not shown) and associated algorithms that are executed by a processor, similar to processor 810. In such implementations, the processor executes the algorithms and filters the input signal acquired from the sensor and perform the classification by identifying patterns associated with different types of motion that can trigger the involuntary leakage/voiding, e.g., laughing, coughing, jumping etc. This information can be wirelessly transferred to the bladder health wristband (e.g., wristband 120), where the motion type is recorded. This motion information may then be correlated to or associated with causes of urinary incontinence, as described in more detail below.

Figure 9:
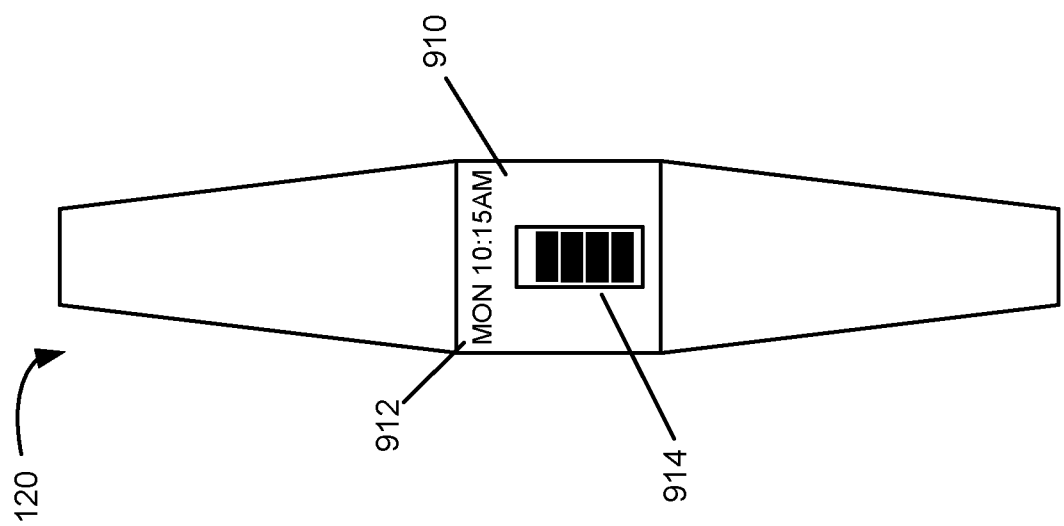
FIG. 9 illustrates the bladder health monitoring wristband of FIG. 1A in accordance with an exemplary implementation.

As described above with respect to FIG. 1A, in one implementation, BVM device 110 may communicate with a wearable computing device, such as wristband 120. In such implementations, the bladder health wristband 120 may include a processor (e.g., ARM microcontroller), an antenna (e.g., Bluetooth or Wi-Fi), a display (e.g., LCD), and a rechargeable battery. Wristband 120 may receive bladder size information from the BVM device 110 via the antenna and display, for example, date, time and a graphic to represent the bladder size. For example, FIG. 9 illustrates an exemplary bladder health wristband 120 with a display area 910. Bladder health wristband 120 may also include a speaker and/or a vibrator for alerts and notifications. Features of wristband 120 may be used in the assessment and management of UI. Referring to FIG. 9, display area 910 may include an area 912 in which the day and time are displayed and an area 914 in which a graphical fullness indicator is displayed. The fullness indicator at area 914 may include a number of bars (e.g., 0-5 bars) with zero bars corresponding to a relatively empty bladder and five bars corresponding to a very full bladder. In the example illustrated in FIG. 9, four bars are illustrated, corresponding to a full or nearly full bladder.

Figure 10:
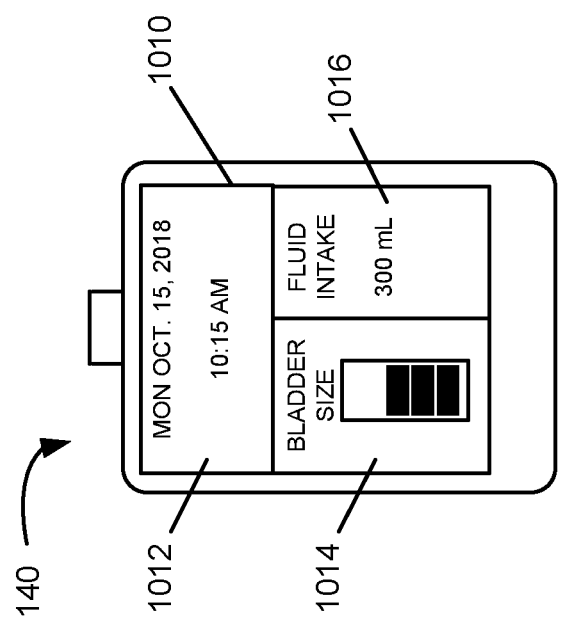
FIG. 10 illustrates the bladder health monitoring display of FIG. 1B in accordance with an exemplary implementation.

As also described above with respect to FIG. 1B, in some implementations, BVM device 110 may communicate with display lanyard 140. In this implementation, bladder health display lanyard 140 includes a display 1010, as illustrated in FIG. 10. Referring to FIG. 10, display 1010 includes area 1012 which displays the time, day and date. Area 1014 graphically illustrates a bladder fullness similar to the graphical indicator at area 914 for wristband 120. Area 1016 illustrates an amount of fluid intake (e.g., in mL or cc). The amount of fluid intake may be obtained by interaction with a monitored drinking cup or other analysis of food/drink intake, described below.

Wristband 120 and display lanyard 140 may each include a processor (e.g., ARM microcontroller), an antenna (e.g., Bluetooth or Wi-Fi), a display (e.g., LCD), a global positioning system (GPS) receiver, and a rechargeable battery (not shown in FIG. 10). In an exemplary implementation, wristband 120 and display lanyard 140 receive (via their respective antennas) bladder size information transmitted wirelessly from BVM device 110. Display lanyard 140 and wristband 120 may each further receive fluid intake information from a "smart" drinking cup (described below) via the antenna. The day, time, a graphic to represent the bladder size/fullness, and fluid intake level can be shown on the display, as illustrated in FIG. 10. Wristband 120 and display lanyard 140 may each also detect and record patient location via a GPS receiver included in wristband 120/lanyard 140. Wristband 120 and display lanyard 140 may each further include a speaker and/or a vibrator for alerts and notifications.

Figure 11:
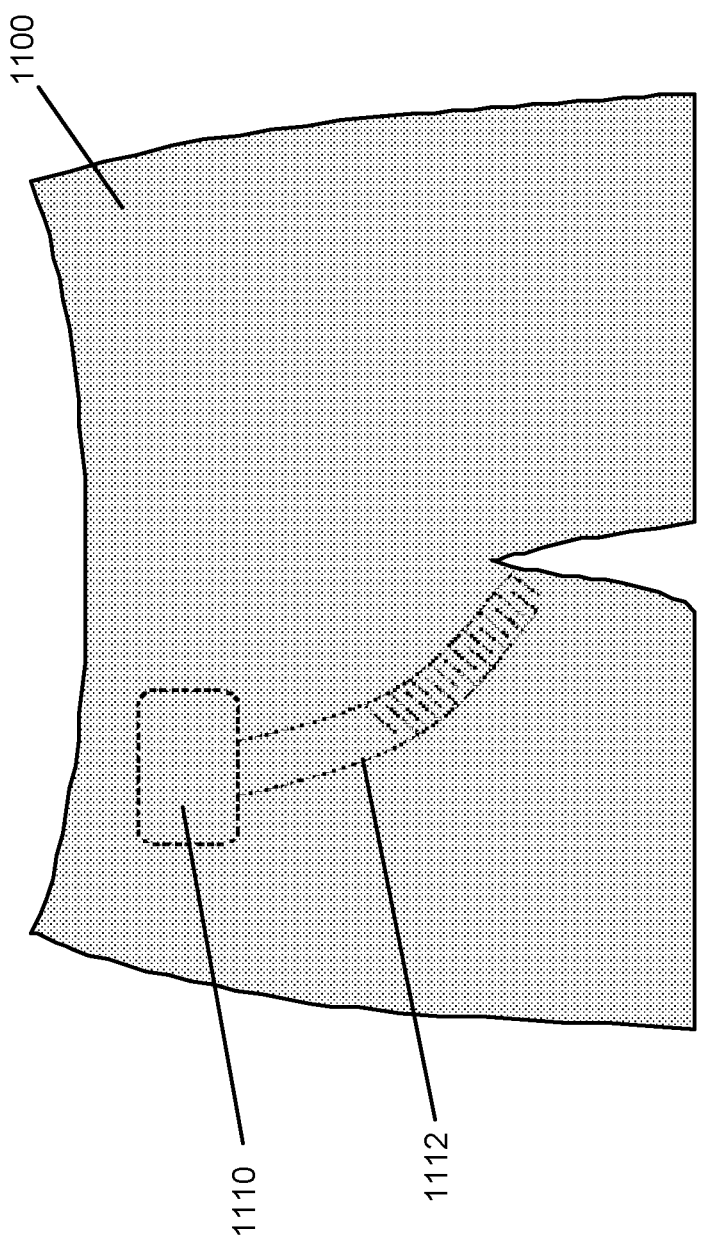
FIG. 11 illustrates an exemplary undergarment with an embedded moisture sensor in accordance with an exemplary implementation.

As described previously, in some implementations, systems and methods described herein may detect moisture associated with patient 100. For example, referring to FIG. 11, patient 100 may wear underwear 1100 or another undergarment that includes an embedded moisture sensor 1110. Sensor 1110 may be used to detect and estimate amount of accidental urine leakage. The shape and/or size of moisture sensor 1110 can vary for men and women, and based on age. In addition, in some implementations, underwear 1100 may include multiple moisture sensors 1110 to further facilitate accurately estimating an amount of urine leakage.

Figure 12:
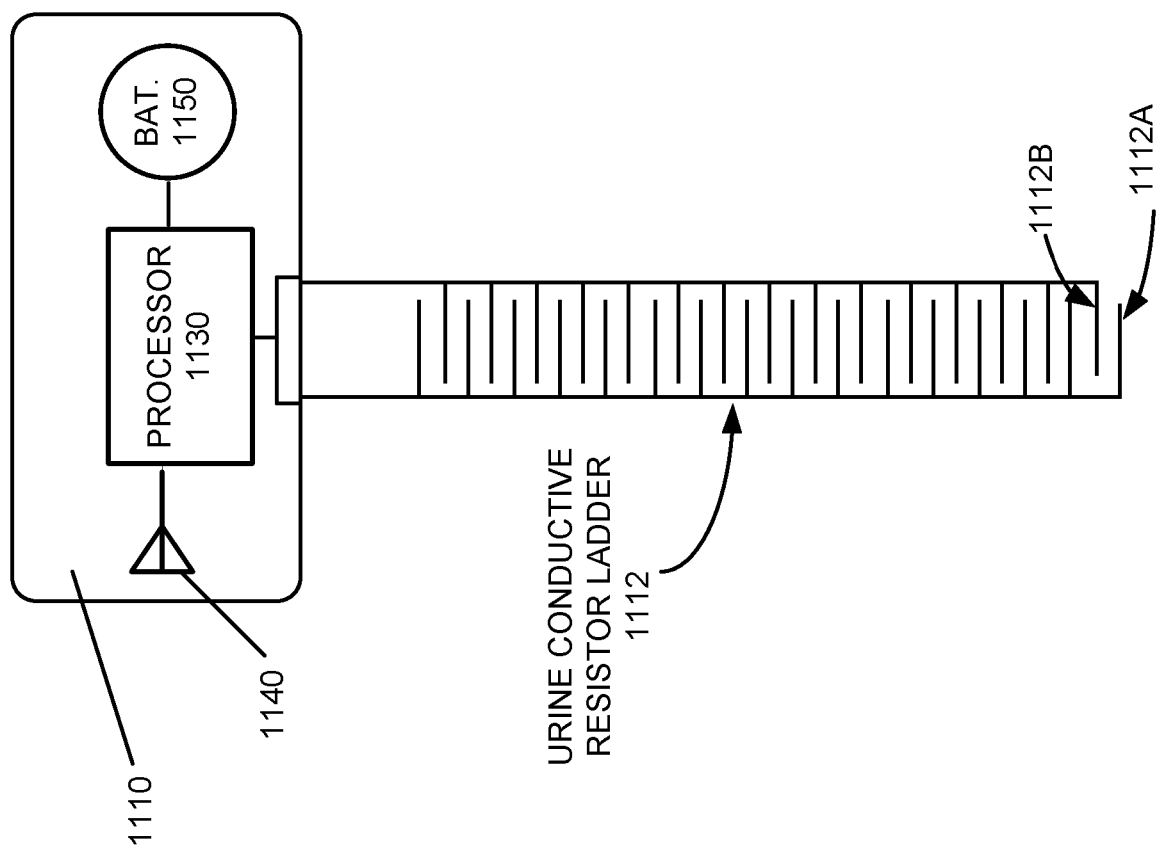
FIG. 12 illustrates components of the moisture sensor of FIG. 11 in accordance with an exemplary implementation.

In one implementation, as illustrated in FIG. 12, moisture sensor 1110 includes a processor 1130 (e.g., ARM microcontroller), resistance/resistor ladder 1112, an antenna 1140 (e.g., Bluetooth), and a battery 1150. Moisture sensor 1110 may also include a water-sealed casing to protect the electronics from fluids, such as urine. Processor 1130 monitors the resistance of resistance ladder 1112. The presence of urine will cause an electrical short between resistance ladder rungs, two of which are labeled 1112A and 1112B in FIG. 12, and reduce the resistance of the resistance ladder 1112. In some examples, larger amounts of urinary leakage will lead to a lower overall resistance due to higher resistance ladder rungs being shorted. In general, a larger urinary leakage will lead to a lower resistance. Information related to detection of an accidental urinary leakage and estimated amount of urinary leakage can be recorded and then transmitted via antenna 1140 to wristband 120/lanyard 140 and/or a remote caregiver.

Figure 13:
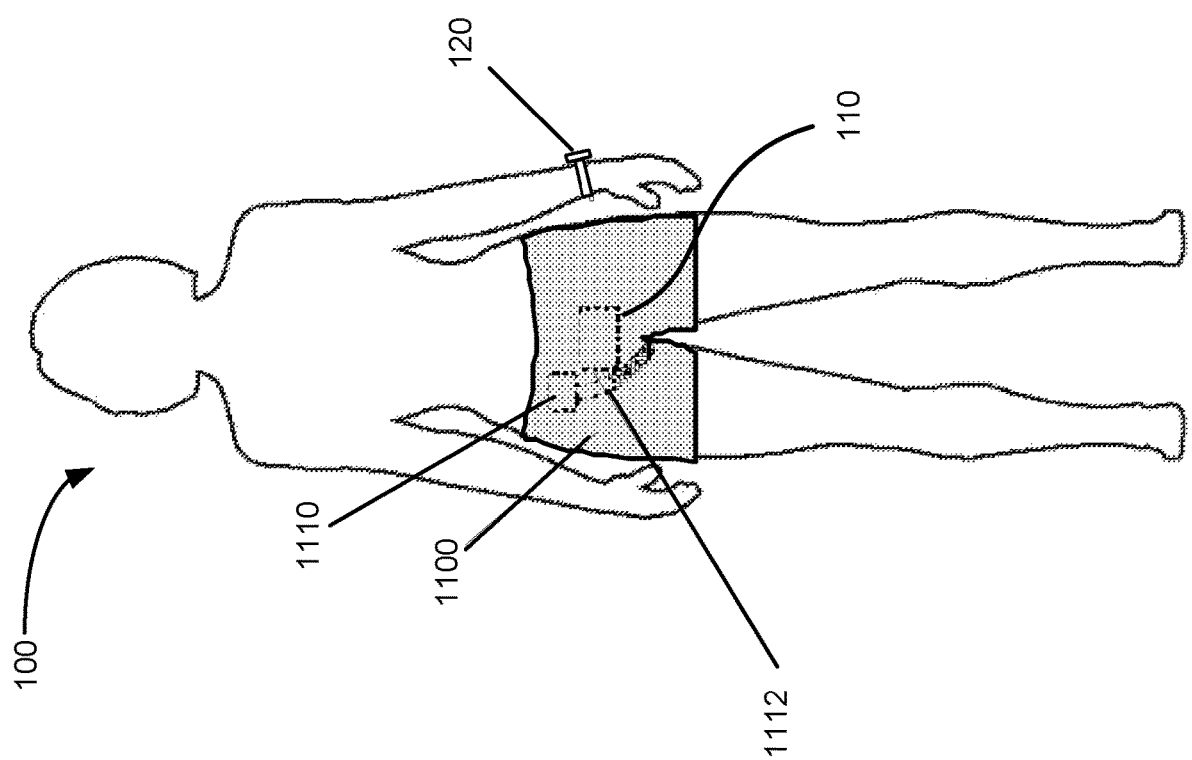
FIG. 13 illustrates an undergarment with an embedded moisture sensor and bladder volume monitoring device worn by a user, along with a bladder health wristband, in accordance with an exemplary implementation.

FIG. 13 illustrates a multi-sensor scenario in which patient 100 has wearable BVM device 110, underwear 1100 with an embedded moisture sensor 1110, and a bladder health wristband 120. The system of sensors illustrated in the multi-sensor system of FIG. 13 may be used to monitor bladder volume, detect and measure amount of accidental urinary leakage, and alert patient to a pre-defined bladder volume level.

Figure 14:
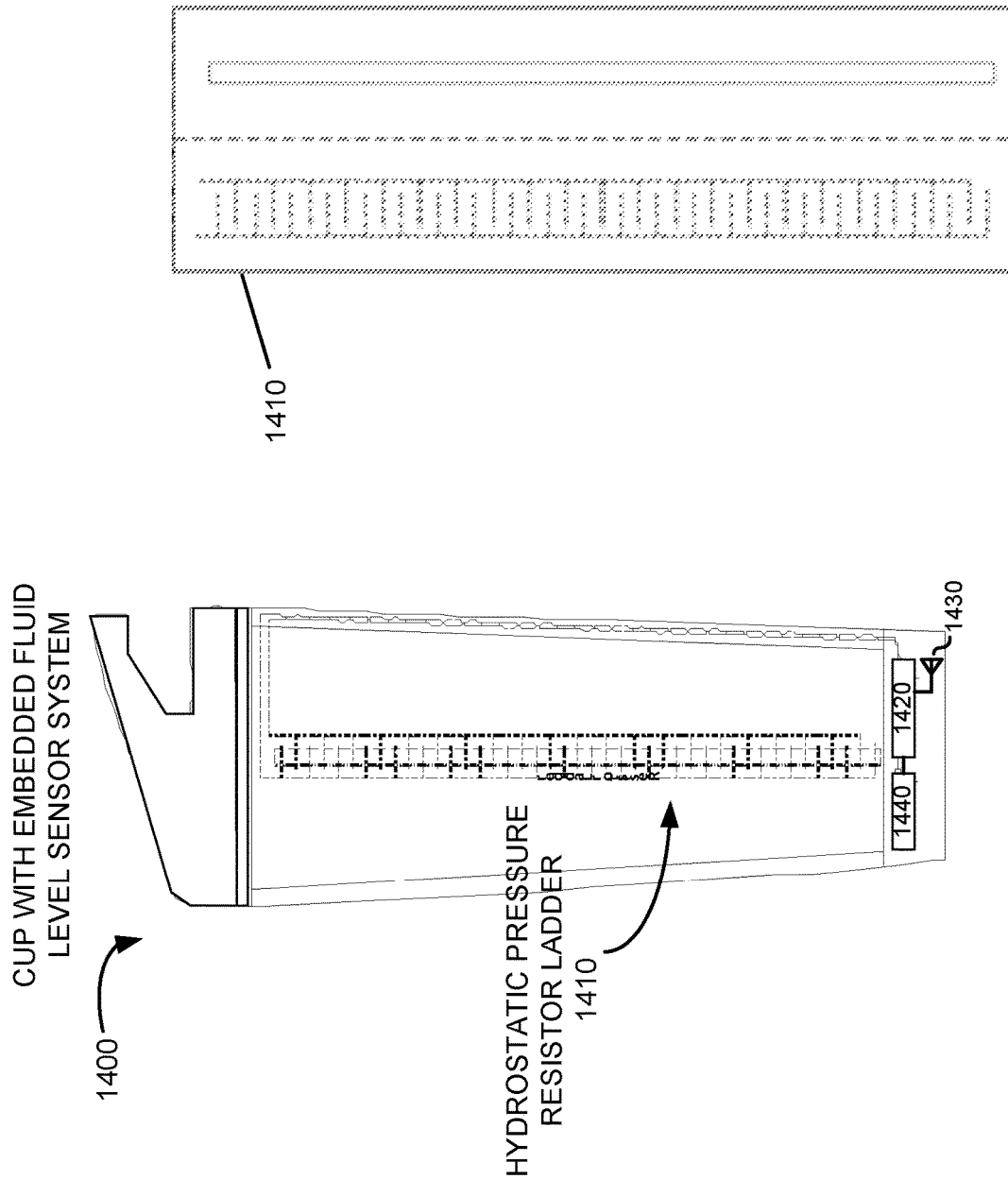
FIG. 14A illustrates an exemplary cup with an embedded fluid level sensor system in accordance with an exemplary implementation.
FIG. 14B illustrates details of a hydrostatic pressure resistor ladder implemented in the cup of FIG. 14A in accordance with an exemplary implementation.

Optimal bladder health typically requires appropriate fluid intake. Use of drinking cups with automated measurement of fluid amount can facilitate recording of fluid intake. For example, FIG. 14A illustrates a sectional side view of a "smart" drinking cup 1400 that may be used in conjunction with implementations described herein. Smart drinking cup 1400 includes a processor 1420 (e.g., ARM microcontroller), an antenna 1430 (e.g., Bluetooth) and a battery 1440, along with sealed resistance/resistor ladder 1410. Resistance ladder 1410 includes electrical conductors on the surface of a foldable substrate (e.g., printed conductive ink on polyimide) in which a first side includes a first pattern of conductors that are not connected and a second side which includes a second pattern of conductors, as illustrated in FIG. 14B. The ladder rungs of the first pattern of conductors become electrically connected by hydrostatic pressure due to fluid, such as water, when the first and second sides of the foldable substrate are in contact with each other. As the fluid level rises, higher level ladder rungs located toward the top of cup 1400 are electrically connected, leading to a lower resistance. The tracking of increasing and decreasing fluid levels can be used to estimate fluid intake of a patient. The fluid intake amount can be transmitted to the patient's bladder health display lanyard 140, wristband 120 and/or to a remote caregiver. Additional details regarding resistor ladder technology is provided by U.S. Pat. No. 7,661,307 by Milone, the contents of which are hereby incorporated herein by reference.

In another implementation associated with a smart drinking cup, a mass or weight scale is integrated into the base of the cup (not shown). The fluid volume can be estimated from the measured mass or weight. In each case, the volume of fluid consumed by a patient can be measure and transmitted to another device (e.g., wristband 120, lanyard 140 or to a caregiver).

Figure 15:
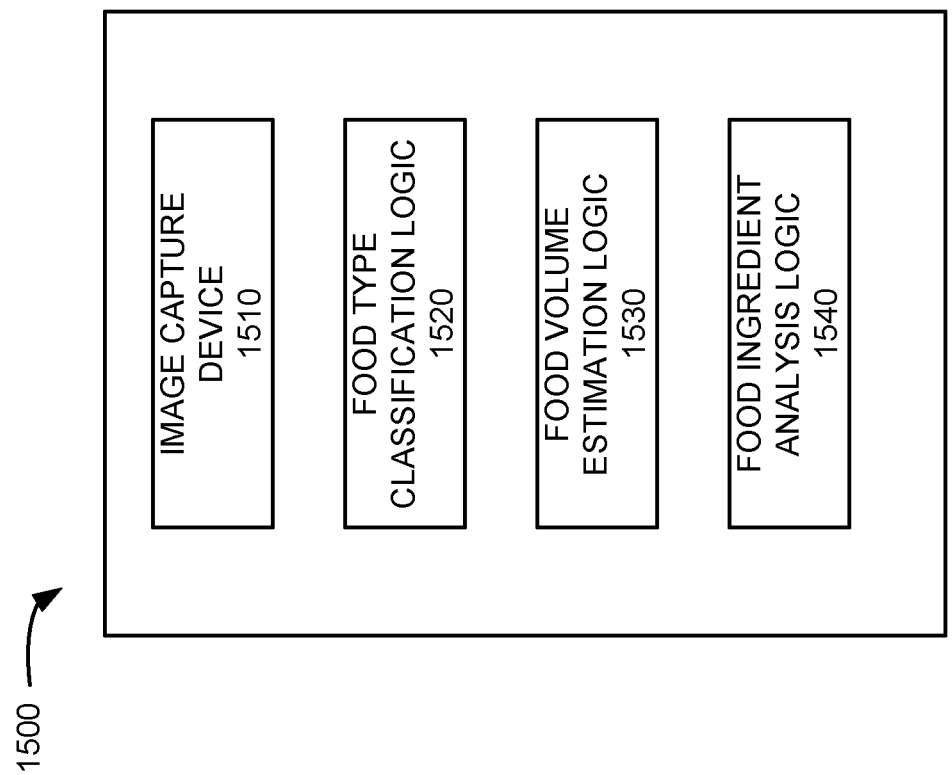
FIG. 15 illustrates an exemplary user device to detect food and beverage type, volume and ingredients in accordance with an exemplary implementation.

As described previously managing urinary incontinence is a difficult task for millions of people. For example, many beverages and foods, e.g., coffee, soda, chocolate and spicy ingredients etc., can irritate the bladder and tend to make kidneys produce more urine and increase the incidence of urinary incontinence. Knowing the type, volume and ingredients of intake drinks and foods plays an important role in helping clinicians to identify the cause of urinary incontinence problems. FIG. 15 illustrates an implementation in which a mobile user device, such as a smart phone may include a software application to classify the food type, perform the volume estimation and analyze the food ingredients.

For example, referring to FIG. 15, user device 1500, which may be a smart phone, or other mobile computing device, such as a wearable computer (e.g., eyeglasses, a wristwatch, etc.), may include an image capture device 1510, food type classification logic 1520, food volume estimation logic 1530 and food ingredient analysis logic 1540. Image capture device 1510 may be a camera associated with user device 1500 (e.g., a camera included in a smart phone) and may be used to capture multiple pictures and/or videos of the food before and after a meal or snack is eaten. Food type classification logic 1520 may classify the food type captured by the image capture device 120. For example, food type classification logic 1520 may classify the food as liquid, solid, vegetable, meat, bread, etc., or generate more specific classifications, such as milk, coffer, hamburger, broccoli, etc. Food volume estimation logic 1530 may estimate the volume of each identified food type consumed by the patient (e.g., in ounces) based on the before and after images, such as analyzing what portion of a full cup of coffee was consumed, a portion of a hamburger that was eaten, etc. The food volume may be used to estimate a liquid content in the foods/drinks that were consumed. Food ingredient analysis logic 1540 may analyze and estimate the ingredients within each identified food type. The ingredient analysis may also be used to estimate, for example, liquid or fluid content in the meal.

In some implementations, a computer vision algorithm (e.g., a convolutional neural network) might be included in food type classification logic 1520 to aid in classifying different types of food. In one implementation, food volume estimation logic 1530 may construct the three-dimensional (3D) model of the food via multiple views of images and/or video frames. The ingredients information of the food can be extracted by first performing the image segmentation and followed by the classification of various food ingredients. The food type, volume and ingredient information can be wirelessly transferred to a database or stored locally in user device 1500 (e.g., in the mobile phone). Combined with other information, such as the date, time, bladder volume measurement and amount of urinary leakage, a detailed bladder diary report may be automatically generated by user device 1500 or an external device and used by urologists for diagnostic purposes.

Although FIG. 15 illustrates analyzing food and beverages using 3D analysis or other image-based analysis, in other implementations, other image-based analysis may be used. For example, image capture device 1510 may capture a Universal Product Code (UPC) associated with a product and use the UPC to retrieve the type, volume and ingredient information.

In situations when the ingredients of beverages and foods cannot be readily captured by a camera, e.g., multiple cups of coffee, the information can be manually input by users via keyboard or voice input associated with user device 1500. In each case, user device 1500 may be used to record food/beverage intake and estimate fluid levels based on the intake. This information may then be used to assess and manage UI, as described in detail below.

Figure 16:
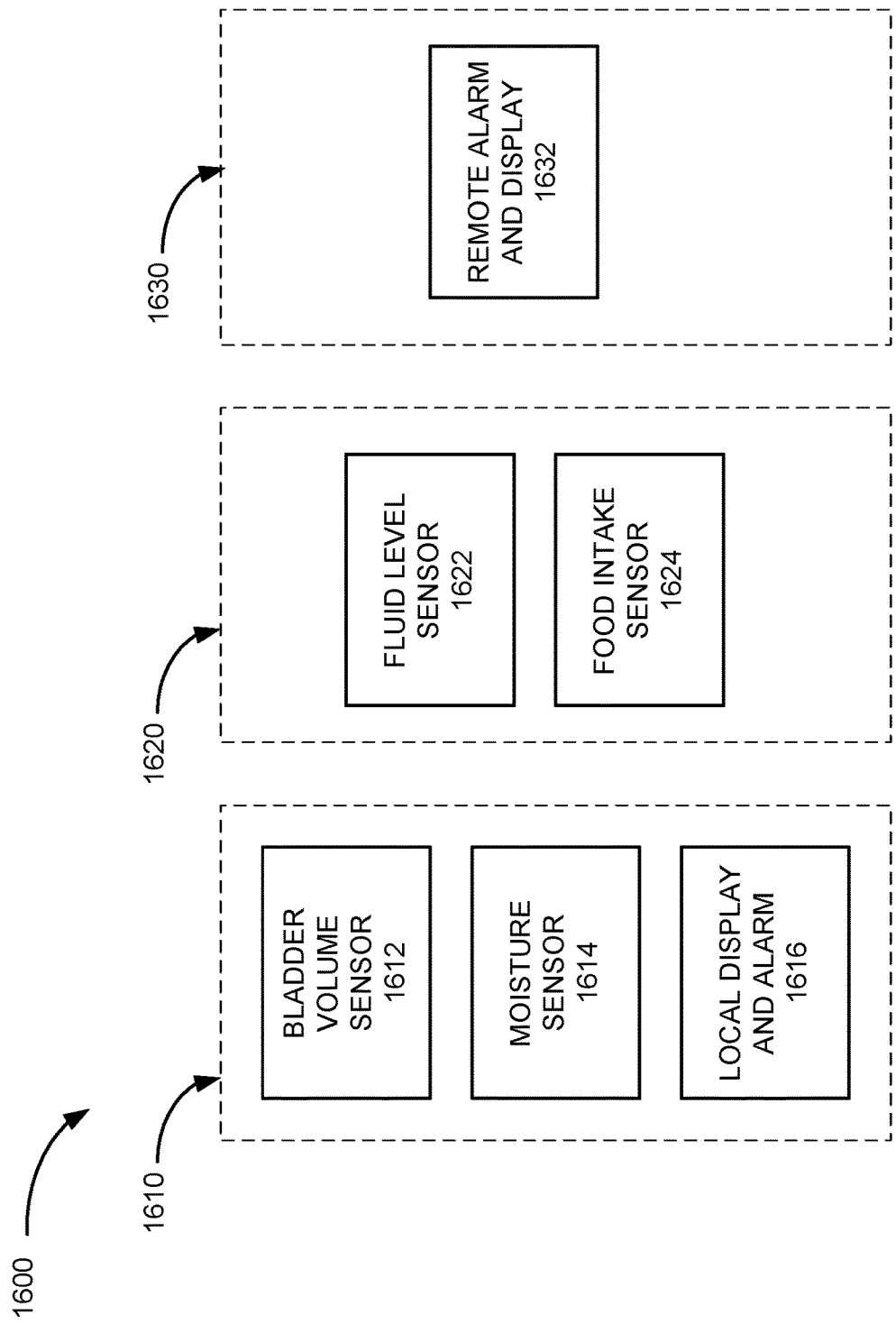
FIG. 16 illustrates a bladder health multi-sensor network in accordance with an exemplary implementation.

FIG. 16 illustrates a diagram of a bladder health multi-sensor network 1600, which includes body sensors 1610, intake sensors 1620, and remote displays 1630. In an exemplary implementation, body sensors 1610 include a bladder volume sensor (e.g., BVM device 110), moisture sensor 1614 (e.g., moisture sensor 1110) and a local display and alarm 1616 (e.g., wristband 120, lanyard 140). Intake sensors 1620 may include a fluid level sensor 1622 (e.g., smart drinking cup 1400), and a food intake sensor 1622 (e.g., user device/smart phone 1500 including a camera). Remote displays 1630 include a remote display and alarm that may alert a caregiver to a voiding event. The bladder health multi-sensor network 1600 is an example of a multi-sensor system that can be used to assess and manage UI.

Exemplary Methods

As described above, managing urinary incontinence can be challenging. However, using a multi-sensor system, such as system 1600, may allow patients to more easily assess and manage their UI. For example, in one exemplary implementation, a multi-sensor system, including a BVM device 110, underwear 1100 with an embedded moisture sensor 1110, a bladder health display lanyard 140, a smart drinking cup 1400, and a smart phone 1500 may be used by a patient 100 to complete a bladder health diary, such as a 3-day bladder record/diary, in order to assess his/her type of UI.

Figure 17:
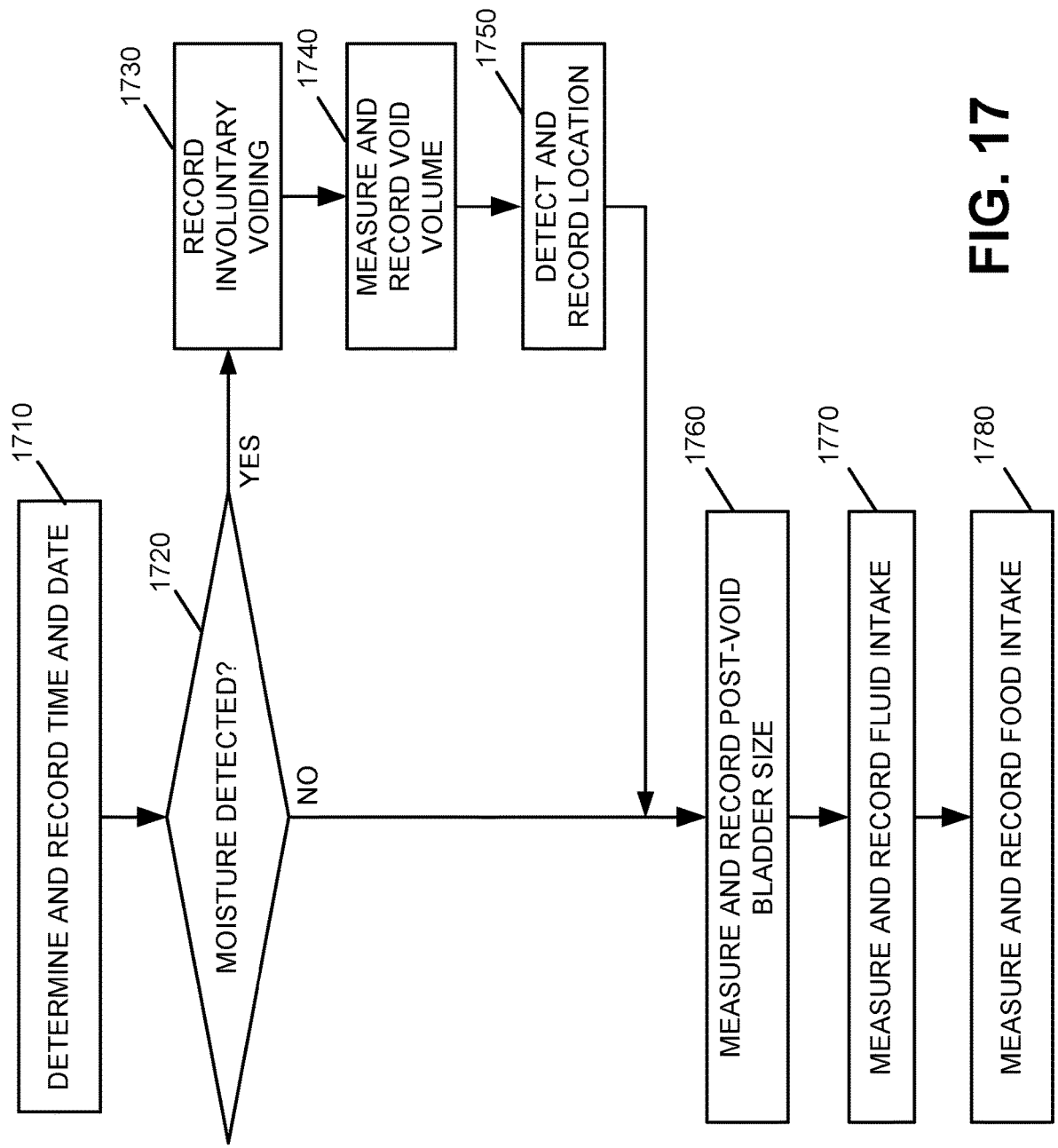
FIG. 17 is a flow diagram illustrating processing associated with a urinary incontinence assessment method in accordance with an exemplary implementation.

FIG. 17 is an exemplary flow diagram illustrating recording data relating to a voiding event. Capturing details of involuntary voiding, as described below, may allow a user or medical personnel to analyze involuntary voiding (or accidental leakage) events to avoid such incidents. In this implementation, the steps illustrated and described below may be repeated for each voiding event during the 3-day assessment.

Processing may begin with determining and recording the date and time (block 1710). For example, the time and date may be read from bladder health display lanyard 140. Underwear 1100 with embedded moisture sensor 1110 may determine whether an involuntary voiding event occurred (block 1720). For example, if moisture is detected (block 1720—yes), an involuntary voiding event is recorded (block 1730), the void size is measured and recorded (block 1740), and the location of the patient is detected and recorded (block 1750). The void size may be a qualitative estimate of small (e.g., enough to make underwear wet if no protective pad worn), moderate (e.g., enough to wet or soak underwear and leak down the legs if no protective pad is worn), or large (e.g., soaks through clothing and onto floor or furniture).

BVM device 110 may measure and record the post-void bladder size (block 1760).

The post-void bladder size may be used to estimate post-void residual amounts of urine in the bladder. Smart drinking cup 1400 may measure and record fluid intake (block 1770). User device 1500 may measure food intake (block 1780). Recording the dates and time of UI events may allow a user or medical personnel to more easily assess the patient's UI and devise particular treatments or regimens for the patient to follow to reduce incidents of UI.

BVM device 110 may transmit details of all voiding event to display lanyard 140. Voiding event details may also be wirelessly transferred to a remote display or system, such as a display associated with a caregiver.

Some UI patients can benefit from a scheduled voiding method where habit training is established by toileting on a rigid, fixed schedule. This type of toileting method may benefit patients in long-term care facilities who are not incontinent more often than, for example, every two hours. All scheduled voiding event details may be recorded to the bladder health display lanyard 140. Scheduled voiding event details may also be wirelessly transferred to a remote display or system.

Figure 18:
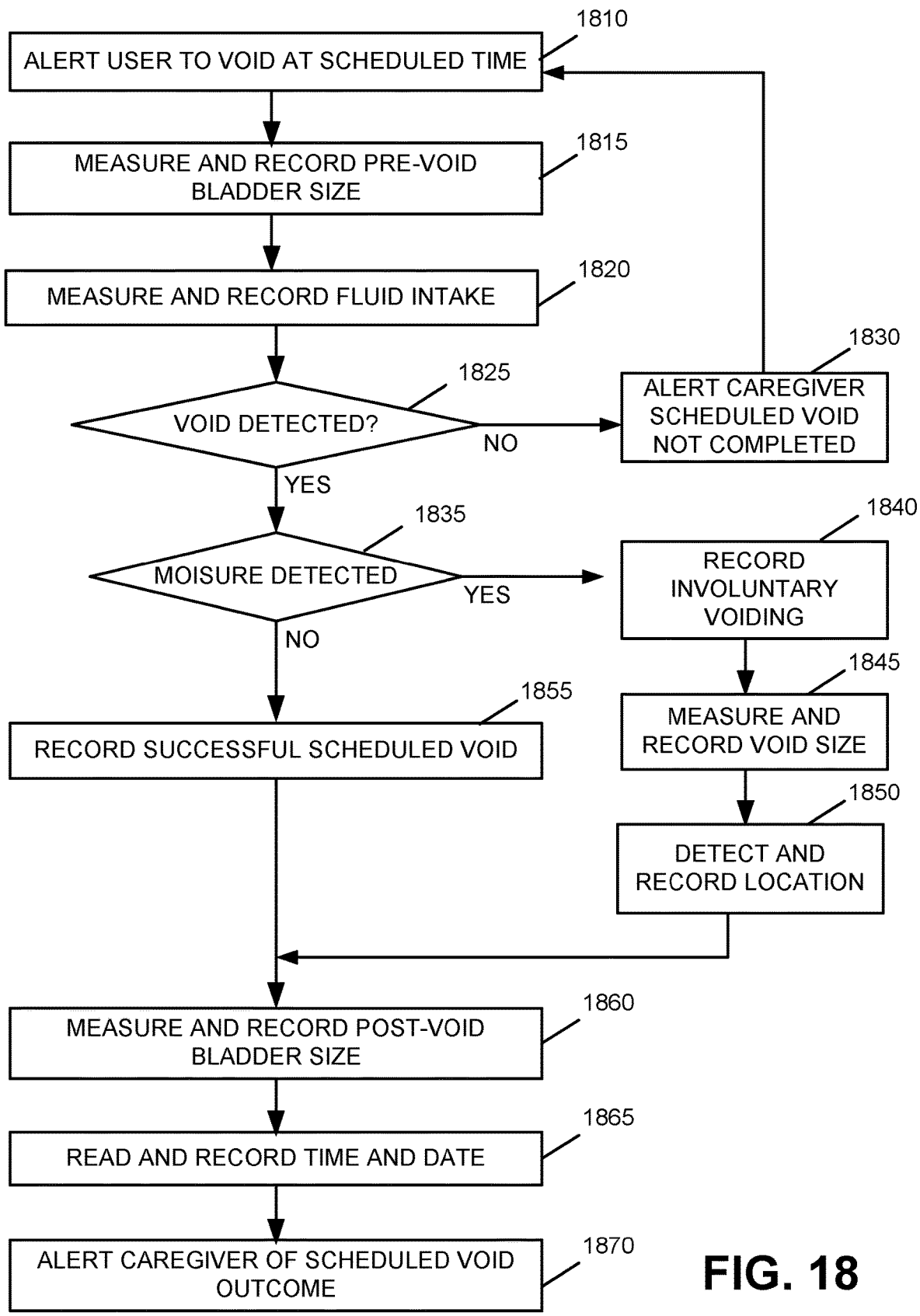
FIG. 18 is a flow diagram illustrating processing associated with a scheduled voiding method in accordance with an exemplary implementation.

FIG. 18 is a flow diagram illustrating a scheduled voiding process in accordance with an exemplary implementation. Processing may begin with bladder health display lanyard 140 alerting the patient to a scheduled void time by an audible alarm and vibration of bladder health display lanyard 140 (block 1810). BVM device 110 may measure the pre-void bladder volume (block 1815). Smart drinking cup 1400 may measure and record fluid intake (block 1815). BVM device 110 may determine if a void is detected (block 1825). If no void is detected by the scheduled void time (block 1825—no), the caregiver is sent an alert that a scheduled void was not completed (block 1830). Processing may then return to block 1810, where the patient is alerted again and pre-void bladder volume and fluid intake are re-recorded. These steps are repeated until a void is detected.

Once a void is detected (block 1825—yes), the multi-sensor system determines whether the void was voluntary or involuntary (block 1835). For example, if moisture is detected by embedded moisture sensor 1110 of underwear 1100, an involuntary voiding event is recorded (block 1840), the void size is measured and recorded (block 1845), and the patient's location is detected and recorded (block 1850). Similar to the UI assessment method, the void size may be a qualitative estimate of small, moderate, or large.

If no moisture is detected (block 1835—no), indicating a voluntary voiding event occurred, a successful scheduling void is recorded (block 1855). The post-void bladder size is measured and recorded (block 1860), and the time and date are read and recorded (block 1865). The caregiver is alerted to outcome of scheduled void event (block 1870). For example, BVM device 110 may send a signal to an external device/system associated with the caregiver indicating the result of the scheduled void.

Some UI patients who are able to recognize urine leakage and are able to respond when prompted can benefit from a prompted voiding program. This type of toileting method may benefit patients who have a bladder capacity of at least 100 mL, have a low number of accidental leakages per day, and can control urination until the toilet is reached.

Figure 19:
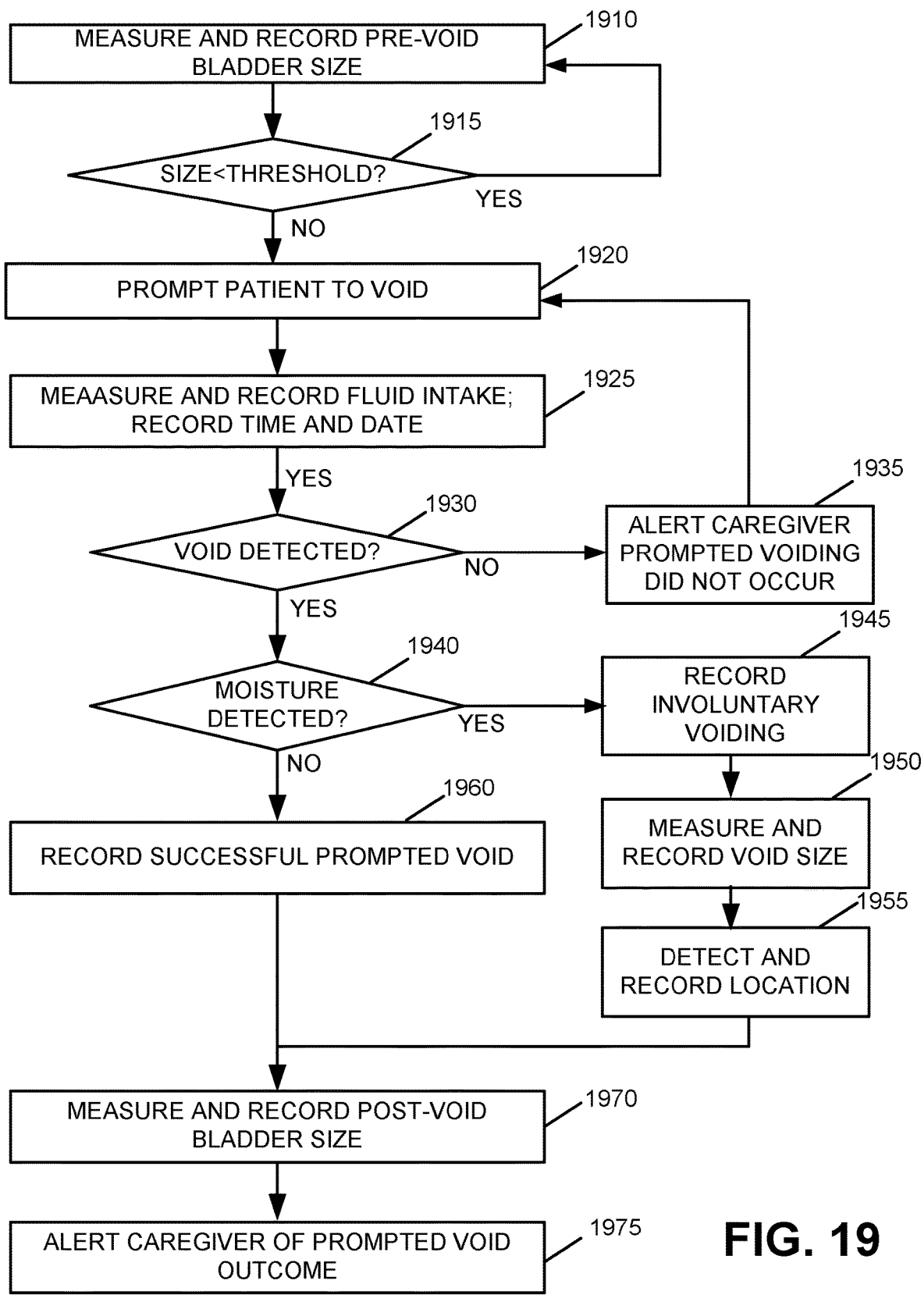
FIG. 19 is a flow diagram illustrating processing associated with a prompted voiding method in accordance with an exemplary implementation.

FIG. 19 illustrates a prompted voiding process in accordance with an exemplary implementation. In this scenario, all scheduled voiding event details may be recorded to bladder health display lanyard 140 or wristband 120. Prompted voiding event details may also be wirelessly transferred to a remote display or system.

Processing may begin with BVM device 110 measuring and recording the patient's pre-void bladder size (block 1910). BVM device 110 may also determine if the pre-void bladder size is less than a predetermined threshold size, such as 150 mL (block 1915). If the bladder size does not exceed the predetermined threshold (block 1915—yes), processing returns to block 1910 and BVM device 110 continues to monitor the bladder size.

If the bladder size exceeds the pre-determined threshold (block 1915—no), bladder health display lanyard 140 may prompt the patient to void (block 1920). For example, BVM device 110 may transmit a signal to display lanyard 140 indicating that the patient is to be prompted to void. Display lanyard 140 receives the signal from BVM device 110 and prompts the patient via, for example, an audible alarm and/or vibration of the bladder health display lanyard 140.

Smart drinking cup 1400 may measure and record fluid intake (block 1925). Smart drinking cup 1400 may also record the date and time and/or display lanyard 140 may record the date and time (block 1925).

BVM device 110 may determine if a void is detected within a predetermined period of time, such as 15 minutes (block 1930). If no void is detected within the predetermined period of time (block 1930—no), an alert that a prompted void was not completed is sent to the caregiver (block 1935). Further, the patient is alerted again and pre-void bladder volume and fluid intake are re-recorded.

Once a void is detected (block 1930—yes), the multi-sensor system determines whether the void was voluntary or involuntary (block 1940). For example, if moisture is detected by the embedded moisture sensor 1110 of underwear 1100 (block 1940—yes), an involuntary voiding event is recorded (block 1945), the void size is measured and recorded (block 1950), and the patient's location is detected and recorded (block 1955). The void size may be a qualitative estimate of small, moderate, or large. If no moisture is detected (block 1940—no), indicating a voluntary voiding event occurred, a successful prompted void is recorded (block 1960). BVM device 110 measures and records the post-void bladder size (block 1970). The caregiver is alerted to outcome of prompted void event (block 1975). In this manner, a patient may be prompted to void based on bladder size, resulting in the reduction of UI incidents. In addition, recording the successful and unsuccessful voiding allows medical personnel to more easily assess the patient's UI. In some implementations, wristband 120 and/or lanyard 140 may be programmed to automatically adjust when alerts to patient 100 is provided based on analyzing previous UI incidents detected by moisture detector 1110 in conjunction with bladder volume information measured by BVM device 110 prior to involuntary voiding. For example, if wristband 120 and/or lanyard 140 determines that involuntary voiding occurs when the bladder size is approximately 100 mL, wristband 120 and/or lanyard 140 may provide an alert to patient 110 when the bladder size is approximately 80 mL, to attempt to avoid a UI incident.

FIG. 20 illustrates an exemplary configuration of a device 2000. Device 2000 may correspond to, for example, a component used in a multi-sensor system, such as BVM device 110, a bladder health display, such as wristband 120 or lanyard 140, moisture sensor 1110, smart phone/user device 1500 or a component of one or more of these devices. Referring to FIG. 20, device 2000 may include bus 2010, processor 2020, memory 2030, input device 2040, output device 2050, communication interface 2060 and global positioning system (GPS) receiver 2070. Bus 2010 may include a path that permits communication among the elements of device 2000. In an exemplary implementation, all or some of the components illustrated in FIG. 20 may be implemented and/or controlled by processor 2020 executing software instructions stored in memory 2030.

Processor 2020 may include one or more processors, microprocessors, processing logic, FPGAs, ASICs, ARM microcontrollers, etc., that may interpret and execute instructions. Memory 2030 may include a random access memory (RAM) or another type of dynamic storage device that may store information and instructions for execution by processor 2020. Memory 2030 may also include a read only memory (ROM) device or another type of static storage device that may store static information and instructions for use by processor 2020. Memory 2030 may further include a solid state drive (SSD). Memory 2030 may also include a magnetic and/or optical recording medium (e.g., a hard disk) and its corresponding drive.

Input device 2040 may include a mechanism that permits a user to input information to device 2000, such as a keyboard, a keypad, a mouse, a pen, a microphone, a touch screen, voice recognition and/or biometric mechanisms, etc. Output device 2050 may include a mechanism that outputs information to the user, including a display (e.g., a liquid crystal display (LCD)), a printer, a speaker, etc. In some implementations, a touch screen display may act as both an input device and an output device.

Communication interface 2060 may include one or more transceivers that device 2000 uses to communicate with other devices via wired, wireless or optical mechanisms. For example, communication interface 2060 may include one or more radio frequency (RF) transmitters, receivers and/or transceivers and one or more antennas for transmitting and receiving RF data via a network. Communication interface 2060 may also include a modem or an Ethernet interface to a LAN or other mechanisms for communicating with elements in a network.

GPS receiver 2070 may include circuitry (e.g., hardware and software) to receive signals from a global positioning system and determine GPS coordinates to determine the location of device 2000.

The exemplary configuration illustrated in FIG. 20 is provided for simplicity. It should be understood that device 2000 may include more or fewer devices than illustrated in FIG. 20. In an exemplary implementation, device 2000 performs operations in response to processor 2020 executing sequences of instructions contained in a computer-readable medium, such as memory 2030. A computer-readable medium may be defined as a physical or logical memory device. The software instructions may be read into memory 2030 from another computer-readable medium (e.g., a hard disk drive (HDD), SSD, etc.), or from another device via communication interface 2060. Alternatively, hard-wired circuitry, such as application specific integrated circuits (ASICs), field programmable gate arrays (FPGAs), etc., may be used in place of or in combination with software instructions to implement processes consistent with the implementations described herein. Thus, implementations described herein are not limited to any specific combination of hardware circuitry and software.

In addition, implementations have been described herein with respect to detecting and monitoring urinary incontinence. In other implementations, implementations described herein may be used to detect/monitor other issues in which bladder control may be an issue. Still further, implementations described herein refer to undergarments that include moisture sensors and/or bladder monitoring devices. In other implementations, other type of garments, such as shorts, tights, athletic wear, clothing liners, etc., may include sensors to detect moisture and sensors to monitor bladder volume.

Further, while series of acts have been described with respect to FIGS. 17-19, the order of the acts may be different in other implementations. Moreover, non-dependent acts may be implemented in parallel.

It will be apparent that various features described above may be implemented in many different forms of software, firmware, and hardware in the implementations illustrated in the figures. The actual software code or specialized control hardware used to implement the various features is not limiting. Thus, the operation and behavior of the features were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as one or more processors, microprocessor, application specific integrated circuits, field programmable gate arrays or other processing logic, software, or a combination of hardware and software.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A system comprising:
   at least one wearable device configured to:
     monitor a bladder volume of a user associated with the at least one wearable device,
     monitor urinary leakage associated with the user, and
     transmit information regarding the bladder volume and urinary leakage; and
   a wearable display device configured to:
     receive the information regarding the bladder volume and urinary leakage from the at least one wearable device, and
     display information to the user based on the received information,
   wherein the at least one wearable device comprises a moisture sensor configured to estimate an amount of urinary leakage, and
   wherein the wearable display device comprises a wristband or a lanyard configured to display the estimated amount of urinary leakage.

2. The system of claim 1, wherein the at least one of the wearable device further comprises a bladder volume monitoring device configured to monitor the bladder volume of the user, and
   wherein the moisture sensor is configured to measure moisture the amount of urinary leakage associated with urinary incontinence.

3. The system of claim 1, wherein the at least one wearable device further comprises:
   an ultrasound device comprising:
     at least one ultrasound transducer configured to transmit ultrasound signals into the user's body and receive echoes of the ultrasound signals,
     a processor configured to analyze the received echo signals and estimate a volume of the user's bladder, and
     a transmitter configured to transmit information identifying the estimated volume.

4. The system of claim 1, wherein the at least one wearable device further comprises:
   a near-infrared device comprising:
     a near-infrared light source,
     a near-infrared light detector,
     a processor configured to analyze signals from the near-infrared light detector and estimate a volume of the user's bladder, and
     a transmitter configured to transmit information identifying the estimated volume.

5. The system of claim 1, wherein the at least one wearable device further comprises:
   a bioelectrical impedance device comprising:
     a radio frequency source, and
     a plurality of excitation electrodes,
     a plurality of measurement electrodes,
     a processor configured to analyze signals from the plurality of measurement electrodes and estimate a volume of the user's bladder, and
     a transmitter configured to transmit information identifying the estimated volume.

6. The system of claim 1, wherein the wearable display device comprises a lanyard worn around the user's neck.

7. The system of claim 6, wherein the wearable display device is further configured to:
   provide at least one of a visible or audible alarm based on the bladder volume.

8. The system of claim 6, wherein the display device is further configured to:
   provide at least one of a visible alarm or an audible alarm based on a time associated with a scheduled voiding event.

9. The system of claim 1, further comprising:
   a mobile device comprising:
     a camera configured to capture images of food and beverage taken before and after the user consumes at least some of the food and beverage;
     a processor configured to
       identify food and beverage types associated with the captured images,
       estimate a quantity of food and beverage consumed by the user, and
       estimate an amount of fluid based on the identified food and beverage types and the estimated quantity of consumed food and beverage;
     a memory configured to store the estimated amount of fluid and a time associated with the user's consumption of the estimated amount of fluid.

10. The system of claim 9, wherein the mobile device further comprises:
    a transmitter configured to transmit the estimated amount of fluid to at least one of the display device or an external device associated with a caregiver of the user.

11. The system of claim 1, further comprising:
    a motion detection device comprising a sensor configured to detect types of motion patterns associated with the user.

12. The system of claim 11, wherein the motion detection device further comprises:
    a processor configured to:
      classify types of motion patterns, and
      correlate the types of motion patters to urinary incontinence incidents.

13. The system of claim 1, wherein the at least one wearable device further comprises:
    an ultrasound device comprising:
      at least one ultrasound transducer configured to transmit ultrasound signals into the user's body, wherein characteristics of the transmitted ultrasound signals are configured to be based on at least one of the user's sex or size, and receive echoes of the ultrasound signals,
      a processor configured to analyze the received echo signals and estimate a volume of the user's bladder, and
      a transmitter configured to transmit information identifying the estimated volume.

14. The system of claim 1, wherein the wearable display device comprises a wristband worn on the user's wrist.

15. The system of claim 1, wherein the moisture sensor comprises a plurality of resistive elements, wherein exposure to moisture reduces a total resistance of the plurality of resistive elements, and wherein the moisture sensor is configured to estimate the amount of the urinary leakage based on the total resistance.

16. A method, comprising:
monitoring a bladder volume of a user associated via a wearable device worn by the user, wherein the monitoring the bladder volume comprises:
  transmitting ultrasound signals into the user's body, wherein characteristics of the transmitted ultrasound signals are configured to be based on at least one of the user's sex or size,
  receiving echoes of the ultrasound signals,
  analyzing the received echo signals, and
  estimating the bladder volume of the user based on the received echo signals;
monitoring urinary leakage associated with urinary incontinence of the user, wherein the monitoring urinary leakage comprises:
  estimating an amount of urinary leakage;
transmitting information regarding the estimated bladder volume and the estimated amount of urinary leakage to a wearable display device;
receiving, by the wearable display device, the estimated bladder volume and the estimated amount of urinary leakage; and
displaying, via the wearable display device, the received estimated bladder volume and estimated amount of urinary leakage.

17. The method of claim 16, wherein the displaying comprises:
displaying a graphical bladder volume fullness indicator.

18. The method of claim 16, wherein the displaying comprises:
displaying text identifying an estimated bladder volume.

19. The method of claim 16, further comprising:
displaying, via the display device, an estimated fluid intake value associated with the user's intake of food and liquids.

20. The method of claim 16, wherein the monitoring a bladder volume via the wearable device comprises monitoring the bladder volume using at least one of ultrasound, a near infrared sensor or bioelectrical impedance.

21. The method of claim 16, wherein the monitoring urinary leakage comprises:
determining a total resistance associated with a plurality of resistive elements, wherein exposure to moisture reduces the total resistance of the plurality of resistive elements, and
estimating the amount of urinary leakage based on a total resistance of the plurality of resistive elements.

* * * * *